(12) United States Patent
Gilmanshin

(10) Patent No.: US 7,977,048 B2
(45) Date of Patent: Jul. 12, 2011

(54) DETECTION AND QUANTIFICATION OF ANALYTES IN SOLUTION USING POLYMERS

(75) Inventor: Rudolf Gilmanshin, Framingham, MA (US)

(73) Assignee: Pathogenetix, Inc., Woburn, MA (US)

( * ) Notice: Subject to any disclaimer, the term of this patent is extended or adjusted under 35 U.S.C. 154(b) by 202 days.

(21) Appl. No.: 11/035,417

(22) Filed: Jan. 13, 2005

(65) Prior Publication Data

US 2005/0153354 A1    Jul. 14, 2005

Related U.S. Application Data

(60) Provisional application No. 60/536,157, filed on Jan. 13, 2004.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 3,645,090 A | 2/1972 | Mochizuki et al. |
| 3,940,475 A | 2/1976 | Gross |
| 4,556,643 A | 12/1985 | Paau et al. |
| 4,737,456 A | 4/1988 | Weng et al. |
| 4,793,705 A | 12/1988 | Shera |
| 4,868,103 A | 9/1989 | Stavrianopoulos et al. |
| 5,190,756 A | 3/1993 | Castellino et al. |
| 5,356,776 A | 10/1994 | Kambara et al. |
| 5,525,465 A | 6/1996 | Haralambidis et al. |
| 5,538,848 A | 7/1996 | Livak et al. |
| 5,654,419 A | 8/1997 | Mathies et al. |
| 5,707,797 A | 1/1998 | Windle |
| 5,795,782 A | 8/1998 | Church et al. |
| 5,837,115 A | 11/1998 | Austin et al. |
| 5,879,625 A | 3/1999 | Roslaniec et al. |
| 5,928,869 A | 7/1999 | Nadeau et al. |
| 6,007,994 A * | 12/1999 | Ward et al. ........................ 435/6 |
| 6,015,714 A | 1/2000 | Baldarelli et al. |
| 6,083,689 A | 7/2000 | Martinelli et al. |
| 6,150,089 A | 11/2000 | Schwartz |
| 6,207,392 B1 | 3/2001 | Weiss et al. |
| 6,210,896 B1 | 4/2001 | Chan |
| 6,225,067 B1 | 5/2001 | Rogers |
| 6,232,066 B1 | 5/2001 | Felder et al. |
| 6,248,537 B1 | 6/2001 | Bensimon et al. |
| 6,263,286 B1 | 7/2001 | Gilmanshin et al. |
| 6,287,765 B1 | 9/2001 | Cubicciotti |
| 6,287,772 B1 | 9/2001 | Stefano et al. |
| 6,294,136 B1 | 9/2001 | Schwartz |
| 6,331,414 B1 | 12/2001 | Lee et al. |
| 6,355,420 B1 | 3/2002 | Chan |
| 6,403,311 B1 | 6/2002 | Chan |
| 6,511,809 B2 | 1/2003 | Baez et al. |
| 6,696,022 B1 | 2/2004 | Chan et al. |
| 6,762,059 B2 | 7/2004 | Wellman et al. |
| 6,772,070 B2 | 8/2004 | Gilmanshin et al. |
| 6,790,071 B2 | 9/2004 | Uezono |
| 6,790,671 B1 | 9/2004 | Austin et al. |
| 6,927,065 B2 | 8/2005 | Chan et al. |
| 7,198,900 B2 | 4/2007 | Woudenberg et al. |
| 7,262,859 B2 | 8/2007 | Larson et al. |
| 7,282,330 B2 | 10/2007 | Zhao et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,595,160 B2 | 9/2009 | White et al. |
| 7,888,011 B2 | 2/2011 | Nilsen et al. |
| 2001/0014850 A1 | 8/2001 | Gilmanshin et al. |
| 2002/0008028 A1 | 1/2002 | Jacobson et al. |
| 2002/0037506 A1 | 3/2002 | Lin et al. |
| 2002/0039737 A1 | 4/2002 | Chan et al. |
| 2002/0051986 A1 | 5/2002 | Baez et al. |
| 2002/0110818 A1 | 8/2002 | Chan |
| 2002/0119455 A1 | 8/2002 | Chan |
| 2002/0187508 A1 | 12/2002 | Wong |
| 2002/0192687 A1 * | 12/2002 | Mirkin et al. ..................... 435/6 |
| 2002/0197639 A1 | 12/2002 | Shia et al. |
| 2003/0059822 A1 | 3/2003 | Chan et al. |
| 2003/0162181 A1 | 8/2003 | Yang et al. |
| 2003/0215864 A1 | 11/2003 | Gilmanshin et al. |
| 2003/0235854 A1 | 12/2003 | Chan |
| 2004/0009612 A1 | 1/2004 | Zhao et al. |
| 2004/0053399 A1 | 3/2004 | Gilmanshin |
| 2004/0166025 A1 | 8/2004 | Chan et al. |
| 2004/0214211 A1 | 10/2004 | Gilmanshin et al. |
| 2004/0235014 A1 | 11/2004 | Nadel et al. |
| 2005/0042665 A1 | 2/2005 | Gilmanshin |
| 2005/0112595 A1 | 5/2005 | Zhao et al. |
| 2005/0112606 A1 | 5/2005 | Fuchs et al. |
| 2005/0112620 A1 | 5/2005 | Chan |
| 2005/0112671 A1 | 5/2005 | Maletta et al. |
| 2005/0123944 A1 | 6/2005 | Neely et al. |
| 2005/0123974 A1 | 6/2005 | Gilmanshin et al. |
| 2005/0142595 A1 | 6/2005 | Maletta et al. |
| 2005/0153354 A1 | 7/2005 | Gilmanshin et al. |
| 2005/0196790 A1 | 9/2005 | Rooke et al. |
| 2005/0221408 A1 | 10/2005 | Nalefski et al. |
| 2006/0078915 A1 | 4/2006 | Fuchs et al. |
| 2006/0134679 A1 | 6/2006 | Larson et al. |
| 2006/0160209 A1 | 7/2006 | Larson et al. |
| 2006/0160231 A1 | 7/2006 | Nadel et al. |

(Continued)

FOREIGN PATENT DOCUMENTS

EP    0 453 301 A2    10/1991

(Continued)

OTHER PUBLICATIONS

Aston et al., Optical mapping and its potential for large-scale sequencing projects. Trends Biotechnol. Jul. 1999;17(7):297-302.

(Continued)

*Primary Examiner* — James Martinell
(74) *Attorney, Agent, or Firm* — Wolf, Greenfield & Sacks, P.C.

(57) ABSTRACT

The invention relates to methods and systems for identifying, quantitating and/or analyzing analytes from samples. The analytes may be organic or inorganic in nature and include but are not limited to pathogens such as viruses.

19 Claims, 6 Drawing Sheets

U.S. PATENT DOCUMENTS

| | | | |
|---|---|---|---|
| 2006/0204978 A1 | 9/2006 | Nilsen et al. | |
| 2006/0228747 A1 | 10/2006 | Fuchs et al. | |
| 2006/0292616 A1 | 12/2006 | Neely et al. | |
| 2006/0292617 A1 | 12/2006 | Neely et al. | |
| 2007/0003950 A1* | 1/2007 | Shen et al. | 435/6 |
| 2007/0042406 A1 | 2/2007 | Yantz et al. | |
| 2007/0128083 A1 | 6/2007 | Yantz et al. | |
| 2007/0166743 A1 | 7/2007 | Gilmanshin | |
| 2008/0003689 A1 | 1/2008 | Lee et al. | |
| 2008/0085552 A1 | 4/2008 | Larson et al. | |
| 2008/0103296 A1 | 5/2008 | Zhao et al. | |
| 2008/0254549 A1 | 10/2008 | Fuchs et al. | |
| 2010/0035247 A1 | 2/2010 | Burton | |
| 2010/0112576 A1 | 5/2010 | Patil | |
| 2010/0116025 A1 | 5/2010 | Gouveia et al. | |
| 2010/0120101 A1 | 5/2010 | Patil et al. | |
| 2010/0294665 A1 | 11/2010 | Allen et al. | |

FOREIGN PATENT DOCUMENTS

| | | |
|---|---|---|
| WO | WO 96/29593 A1 | 9/1996 |
| WO | WO 96/30508 A1 | 10/1996 |
| WO | WO 97/00446 A1 | 1/1997 |
| WO | WO 98/10097 A1 | 3/1998 |
| WO | WO 98/35012 A2 | 8/1998 |
| WO | WO 99/05315 A2 | 2/1999 |
| WO | WO 00/09757 A1 | 2/2000 |
| WO | WO 00/60072 A1 | 10/2000 |
| WO | WO 00/60114 A2 | 10/2000 |
| WO | WO 01/13088 A1 | 2/2001 |
| WO | WO 01/61037 A1 | 8/2001 |
| WO | WO 02/099398 A1 | 12/2002 |
| WO | WO 02/101095 A1 | 12/2002 |
| WO | WO 02/101353 A2 | 12/2002 |
| WO | WO 03/003810 A2 | 1/2003 |
| WO | WO 03/025540 A2 | 3/2003 |
| WO | WO 03/083435 A2 | 10/2003 |
| WO | WO 03/091455 A1 | 11/2003 |
| WO | WO 03/100101 A1 | 12/2003 |
| WO | WO 2004/007692 A2 | 1/2004 |
| WO | WO 2004/048514 A2 | 6/2004 |
| WO | WO 2004/066185 A1 | 8/2004 |
| WO | WO 2004/091795 A2 | 10/2004 |
| WO | WO 2005/012575 A1 | 2/2005 |
| WO | WO 2005/017205 A2 | 2/2005 |
| WO | WO 2005/022162 A1 | 3/2005 |
| WO | WO 2007/056250 A2 | 5/2007 |
| WO | WO 2007/098279 A2 | 8/2007 |
| WO | WO 2008/024483 A1 | 2/2008 |
| WO | WO 2008/085991 A2 | 7/2008 |
| WO | WO 2008/111959 A2 | 9/2008 |
| WO | WO 2009/009127 A2 | 1/2009 |

OTHER PUBLICATIONS

Bensimon et al., Alignment and sensitive detection of DNA by a moving interface. Science. Sep. 30, 1994;265(5181):2096-8. Abstract Only.

Dittrich et al., Sorting of cells and single particles in microstructures. Biophys J. Feb. 24, 2002;82(1):43a, 209-Pos.

Eigen et al., Sorting single molecules: Application to diagnostics and evolutionary biotechnology. Proc Natl Acad Sci U S A. Jun. 21, 1994;91(13):5740-7.

Herrick et al., H Imaging of single DNA molecule: applications to high-resolution genomic studies. Chromosome Res. 1999; 7(6):409-423.

Jing et al., Automated high resolution optical mapping using arrayed, fluid-fixed DNA molecules. Proc Natl Acad Sci U S A. Jul. 7, 1998;95(14):8046-51.

McBride et al., Multiplexed liquid arrays for simultaneous detection of simulants of biological warfare agents. Anal Chem. Apr. 15, 2003;75(8):1924-30. Abstract Only.

Meng et al., Optical mappling of lambda bacteriophage clones using restriction endonucleases. Nat Genet. Apr. 9, 1995;9(4):432-8.

Otobe et al., Behavior of DNA fibers stretched by precise meniscus motion control. Nucleic Acids Res. Nov. 15, 2001;29(22):E109, 6 pages.

Schwartz et al., Separation of yeast chromosome-sized DNAs by pulsed field gradient gel electrophoresis. Cell. May 1984;37(1):67-75. Abstract Only.

Schwartz et al., Ordered restriction maps of Saccharomyces cerevisiae chromosomes contructed by optical mapping. Science. Oct. 1, 1993;262(5130):110-4. Abstract Only.

Van Oss et al., Kinetics and energetics of specific intermolecular interactions. J Mol Recognit. Sep.-Oct. 10, 1997;(5):203-16. Abstract Only.

Ambrose et al., Application of single molecule detection to DNA sequencing and sizing, Ber. Bunsenges. Phys. Chem. 1993; 97:1535-1542.

Caplin et al., LightCycler hybridization probes: the most direct way to monitor PCR amplification for quantification and mutation detection. Biochemica. 1999;1:5-8.

Castro et al., Single-Molecule Electrophoresis: Applications to Biomolecular Detection. SPIE. 1995; 2396:79-85.

Chan et al., DNA mapping using microfluidic stretching and single-molecule detection of fluorescent site-specific tags. Genome Res. Jun. 2004;14(6):1137-46.

Ekstrøm et al., Two-point fluorescence detection and automated fraction collection applied to constant denaturant capillary electrophoresis. Biotechniques. Sep. 2000;29(3):582-4, 586-9.

Gaines et al., A new method for measuring lymphoproliferation at the single-cell level in whole blood cultures by flow cytometry. J Immunol Methods. Sep. 9, 1996;195(1-2):63-72.

Kasianowicz et al., Polymer transport in the alpha-hemolysin ion channel. p. 111. Abstract 26.

Kasianowicz et al., Characterization of individual polynucleotide molecules using a membrane channel. Proc Natl Acad Sci U S A. Nov. 26, 1996;93(24):13770-3.

Kinjo et al., Ultrasensitive hybridization analysis using fluorescence correlation spectroscopy. Nucleic Acids Res. May 25, 1995;23(10):1795-9.

Korn et al., Gene expression analysis using single molecule detection. Nucleic Acids Res. Aug. 15, 2003;31(16):e89. 8 pages.

Lee et al., Laser-induced fluorescence detection of a single molecule in a capillary. Anal Chem. Dec. 1, 1994;66(23):4142-9.

Mertz et al., Single-molecule detection by two-photon-excited fluorescence. Optics Letts. Dec. 15, 1995;20(24):2532-4.

Nie et al., Probing individual molecules with confocal fluorescence microscopy. Science. Nov. 11, 1994;266(5187):1018-21.

Parra et al. High resolution visual mapping of stretched DNA by fluorescent hybridization. Nat Genet. Sep. 1993:5(1):17-21. Abstract Only.

Peck et al., Single-molecule fluorescence detection: autocorrelation criterion and experimental realization with phycoerythrin. Proc Natl Acad Sci U S A. Jun. 1989;86(11):4087-91.

Saffran et al., Site-directed psoralen crosslinking of DNA. Proc Natl Acad Sci U S A. Aug. 1982;79(15):4594-8.

Shera et al., Detection of single fluorescent molecules. Chem Phys Letts. 1990; 174(6): 553-7.

Shortreed et al., High-throughput single-molecule DNA screening based on electrophoresis. Anal Chem. Jul. 1, 2000;72(13):2879-85.

Wang et al., Fluorescence resonance energy transfer between donor-acceptor pair on two oligonucleotides hybridized adjacently to DNA template. Biopolymers. 2003;72(6):401-12.

Xu et al., Multiplexed SNP genotyping using the Qbead system: A quantum dot-encoded microsphere-based assay. Nucleic Acids Res. Apr. 15, 2003;31(8):E43-1-E43-10.

Lewin et al., Gene Expression, vol. 2, 1974, John Wiley & Sons, New York, pp. 148-153.

Landegren et al., Padlock and proximity probes for in situ and array-based analyses: tools for the post-genomic era. Comparative and Functional Genomics. 2003;4:525-530.

Taussig et al., Progress in antibody arrays. Drug Discovery Today: Targets. 2003;2(4):169-176.

Kasianowicz., Polymer transport in the alpha-hemolysin ion channel. p. 111. Abstract 26, Publication name and publication date unavailable.

D'Antoni et al., Single Molecule Detection of Proteins Using Microfluidic Fluorescence Detection. ORC Poster. Apr. 2006.

Iannone et al., Multiplexed single nucleotide polymorphism genotyping by oligonucleotide ligation and flow cytometry. Cytometry. Feb. 1, 2000;39(2):131-40. Abstract Only.

Jo et al., A single-molecule barcoding system using nanoslits for DNA analysis. Proc Natl Acad Sci U S A. Feb. 20, 2007;104(8):2673-8. Epub Feb. 12, 2007.

Larson et al., Single DNA molecule stretching in sudden mixed shear and elongational microflows. Lab Chip. 2006;6(9):1187-1199.

Papkov et al., A single-molecule system for detection and quantification of proteins with robust capture units and potential for high multiplexing. Biophysical Society 53$^{rd}$ Annual Meeting. Feb. 28-Mar. 4, 2009. Boston.

Phillips et al., Application of single molecule technology to rapidly map long DNA and study the confirmation of stretched DNA. Nuc Acids Res. 2005;33(18):5829-5837.

* cited by examiner

DETECTION AND QUANTIFICATION OF ANALYTES IN SOLUTION USING POLYMERS

RELATED APPLICATIONS

This application claims priority to U.S. Provisional Application Ser. No. 60/536,157, entitled "DETECTION AND QUANTIFICATION OF TARGETS IN SOLUTION USING NUCLEIC ACID MAPPING", filed Jan. 13, 2004, the entire contents of which are incorporated by reference herein.

FIELD OF THE INVENTION

The invention relates, inter alia, to detection and quantitation of analytes from samples.

BACKGROUND OF THE INVENTION

Multiplexing refers to the ability to analyze (e.g., detect) more than one, and preferably many, different substances simultaneously. The ability to perform a multiplexed analysis would be advantageous to a number of applications such as proteomics, clinical analysis of body fluids, biodefense, and the like. Applications involving a limited amount of sample or a low concentration of the substances to be detected particularly benefit from multiplexing capability. To be useful, multiplexing systems should demonstrate a high sensitivity, a wide dynamic range, and significant multiplexing capability.

Assays using Luminex® beads in liquid arrays reportedly provide multiplexing of 100 and detect protein at a concentration as low as 10 pM [1]. This bead-based system can also reportedly detect pathogens such as bacteria and viruses. This system can interrogate several thousands of beads per second using a Luminex® LX-100 flow cytometer (Luminex Corp., Austin, Tex.). Collecting sufficient information on approximately 100 different types of beads is reportedly estimated to take about fifteen seconds [1]. However, overall analysis time is limited by the interaction of bead-immobilized antibodies with their respective antigens (i.e., the binding time). The binding time is estimated to be at least 30 minutes and can be even longer if higher sensitivity is required.

There exists a need for a system that provides faster analysis without compromising sensitivity, dynamic range and multiplexing capacity.

SUMMARY OF THE INVENTION

The invention relates generally to analysis of analytes within samples using polymer based methods and compositions. The invention is capable of detecting, quantifying and also harvesting and further analyzing analytes in a sample. The methods and compositions relate to the use of polymers which serve as both scaffolds for analyte-specific binding partners and as unique identifiers for each sought after analyte. A high degree of multiplexing is possible given the diversity in available polymers and analyte-specific binding partners.

Thus, in one aspect, the invention provides a method for detecting an analyte in a sample comprising contacting a sample with a polymer having bound to it an analyte-specific binding partner, detecting binding of an analyte to the analyte-specific binding partner, and determining a labeling pattern of the polymer, wherein the labeling pattern of the polymer indicates the identity of the analyte.

In one embodiment, the analyte is a plurality of analytes, the polymer is a plurality of polymers, and the analyte-specific partner is a plurality of analyte-specific polymers. The polymer may be a nucleic acid, such as a DNA or RNA. It may be naturally occurring or non-naturally occurring.

The primary analyte-specific binding partner may be a nucleic acid or a peptide or protein, but it is not so limited. In one embodiment, the analyte-specific binding partner is an antibody or an antigen-binding antibody fragment.

In one embodiment, the analyte and/or the binding of the analyte to the (primary) analyte-specific binding partner is detected using a secondary analyte-specific binding partner. The secondary analyte-specific binding partner may be a nucleic acid or a peptide or protein, but it is not so limited. In one embodiment, the secondary analyte-specific binding partner is an antibody or an antigen-binding antibody fragment. The secondary analyte-specific binding partner may be identical to the primary analyte-specific binding partner. The secondary analyte-specific binding partner may be conjugated to a detectable label.

In one embodiment, the (primary) analyte-specific binding partner and the secondary analyte-specific binding partner is each labeled with a member of a FRET fluorophore pair (i.e., one is labeled with a FRET donor fluorophore and the other is labeled with a FRET acceptor fluorophore).

In another embodiment, the analyte is directly detectable and binding of the analyte to the analyte-specific binding partner is directly detected.

In one embodiment, the labeling pattern of the polymer is a binding pattern of one or more sequence-specific probes to the polymer. The one or more sequence-specific probes may be conjugated to detectable labels. In another embodiment, the labeling pattern of the polymer is a pattern of detectable labels incorporated into the polymer. The labeling pattern may alternatively be a unique detectable label incorporated into the polymer or a probe bound thereto or conjugated to a probe.

In one embodiment, the method further comprises quantifying analyte concentration in the sample by determining an amount of analyte bound to analyte-specific binding partner and comparing with a standard calibration curve.

In another embodiment, the method further comprises harvesting an analyte-bound polymer and/or optionally analyzing the analyte bound to the polymer via the analyte-specific binding partner.

The analyte may be a nucleic acid, a carbohydrate, a protein, a peptide, a lipid, a toxin, a cell, a spore, a cellular fragment or a spore fragment, although it is not so limited.

In one embodiment, the polymer is elongated prior to or simultaneously with determining the labeling pattern of the polymer.

In another embodiment, the labeling pattern of the polymer is a spatial pattern (or location) of (primary) analyte-specific binding partners bound to the polymer.

In one embodiment, the labeling pattern of the polymer is determined using a focused flow through an electric field. The focused flow through an electric field may also be used to detect the analyte-specific signal whether from the analyte itself or from a secondary analyte-specific binding partner.

In another aspect, the invention provides a composition comprising a polymer bound to one or more analyte-specific binding partners and having a unique label, wherein the unique label is comprised of one or more incorporated detectable labels, one or more bound detectable sequence-specific probes, or one or more bound detectable analyte-specific binding partners. Many of the embodiments recited above apply equally to this aspect of the invention as would be apparent to one of ordinary skill in the art.

These and other embodiments of the invention will be described in greater detail herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and/or the arrangement of components set forth in the following description or illustrated in the drawings. The invention is capable of other embodiments and of being practiced or of being carried out in various ways.

The phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

Figure 1A:
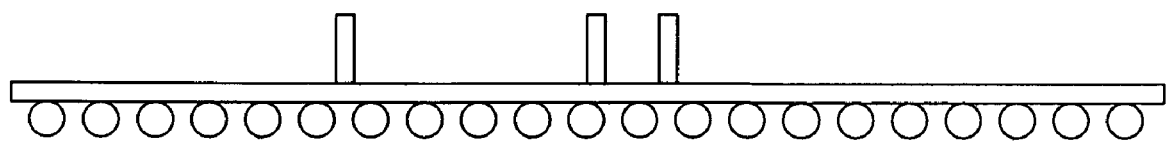
FIGS. 1A, 1B, and 1C each illustrates a polymer (horizontal line) having a bar code (vertical lines) and primary and optionally secondary analyte-specific binding partners (circles) bound thereto.

The Figures are illustrative only and are not required for enablement of the invention.

DETAILED DESCRIPTION OF THE INVENTION

The invention provides in its broadest sense a system for detecting one or more analytes from a sample. The invention employs polymers that are conjugated to analyte-specific binding partners. Each analyte to be detected has a corresponding polymer which is identified by a unique bar code. The unique bar code of the polymer indicates the analyte specificity of the binding partner bound thereto and thus the identity of the analyte.

The method is particularly suited to determining analyte content in a sample wherein the sample is rare or the analyte concentration is low. The invention allows more than one and preferably several different analytes to be detected simultaneously, thereby conserving sample. In other words, the method is capable of a high degree of multiplexing. The degree of multiplexing will depend on the particular application and the number of analytes to be detected. For example, the degree of multiplexing may be 2 (i.e., 2 analytes can be detected in a single analysis), 3, 4, 5, 6, 7, 8, 9, 10, at least 20, at least 50, at least 100, at least 500, or higher.

The degree of multiplexing also appears to be limited by the throughput rate of the specific detection/interrogation system used. The detection/interrogation system may be a single molecule detection system, and more particularly a single molecule linear detection system. The system described in the Examples (i.e., GeneEngine™) appears to be 1000 fold more sensitive than the Luminex® system discussed herein at a multiplexing of 100. The Examples provide a detailed comparison of the parameters of this system and the Luminex® liquid array platform.

The polymer as used herein is any molecule capable of being elongated, conjugated to binding partners, and uniquely labeled. Thus, the polymer may be nucleic acid, amino acid, carbohydrate or lipid in nature, but it is not so limited. In an important embodiment, the polymer is a nucleic acid, whether naturally occurring or not. The nucleic acid may be naturally or non-naturally occurring DNA or RNA, such as genomic DNA, mitochondrial DNA, mRNA, cDNA, rRNA, mRNA, PNA or LNA, or a combination thereof, as described herein. Non-naturally occurring polymers such as bacterial artificial chromosomes (BACs) and yeast artificial chromosomes (YACs) can also be used. Preferably, a non-naturally occurring polymer (e.g., synthesized DNA) is used in order to control mapping and conjugation to analyte-specific binding partners. Harvest and isolation of nucleic acids are routinely performed in the art and suitable methods can be found in standard molecular biology textbooks. (See, for example, Maniatis' Handbook of Molecular Biology.)

It is important that the polymer be uniquely labeled since this label is used to identify a particular analyte. This unique labeling pattern of the polymer is referred to herein as the barcode. The labeling pattern or barcode is one or more detectable (and in some instances unique) labels present on or in a polymer, which uniquely identify that polymer (as well as others identical to it that bind an identical analyte via an analyte-specific binding partner). Each labeling pattern or barcode is associated with one analyte. The labeling pattern or barcode may be a spatial pattern of detectable labels incorporated into the polymer during synthesis. Alternatively, it may be a binding pattern of one or more sequence-specific or structure-specific probes. The probes are detectable either intrinsically or via conjugation to detectable labels. In yet another embodiment, the bar code is comprised of the binding pattern of analyte-specific binding partners. These binding partners may be the same ones used to detect the analyte of interest or they may be specific for a ubiquitous analyte. In this latter instance, the ubiquitous analyte binds to its respective binding partner, and is either directly or indirectly detected. In either case, its signal should be distinguishable from that of the other analyte-specific binding partners on the same polymer. Preferably, however, when this conformation is used, the binding partners have dual functionality: they act as both analyte sensors and as unique labels for the polymer. Such a conformation reduces the steps required to detect analytes since there would be no need for additional polymer labeling.

If determining the barcode requires contacting the polymer with probes, such probes may be added prior to, simultaneously with, or following the addition of the polymer to a sample. That is, the polymer may be labeled before, during or after binding of the analyte-specific binding partners to their respective analytes, provided that the conditions for binding of any of these pairs does not disrupt any of the other binding interactions.

The polymer therefore has dual functionality also. First, it acts as an surrogate marker for the analyte being detected. Second, it is a scaffold for analyte-specific binding partners. Each polymer is associated with a particular analyte binding specificity. It is therefore possible to determine the analyte binding capacity of a polymer by "reading" its barcode. Presence of an analyte will then be determined based on the presence of an analyte-specific signal (such as a detectable label conjugated to a secondary analyte-specific binding partner) and the unique polymer bar code. As will be discussed herein, in instances where a secondary analyte-specific binding partner is used to detect analyte, it is possible that all secondary binding partners are conjugated to the same detectable label. This is because such a label merely indicates that the analyte is present with the polymer barcode indicating the exact identity of the analyte. This eliminates the need for a variety of labels, each specific for a different analyte.

In some embodiments, it is preferred that the polymer be flexible. This is the case with nucleic acids such as DNA which normally exists as a random coil and is stretched only during the interrogation. Stretching the DNA during interrogation enables a higher degree of multiplexing since each polymer can be distinguished based on the relative spatial location of probes or detectable labels. Stretching is not required however during probe or analyte-specific binding partner incubation since the small size of the random coil facilitates faster diffusion rates and therefore reduces incubation time. This is described in greater detail in the Examples.

The invention further contemplates analysis of polymers in a compact, non-elongated form. This can be useful if each polymer labeling pattern is uniquely detected irrespective of spatial location of probes or detectable labels. For example, it is possible that each analyte-specific polymer is labeled with a unique label and the presence of the label regardless of its position along the length of the polymer is used to identify the polymer (and consequently the analyte bound thereto). This approach will be best suited to applications that do not require extensive multiplexing. It should be understood that this approach will therefore not require a linear analysis system nor will it require elongation of the polymer prior to or during interrogation.

A binding partner as used herein is a compound that binds to an analyte with a desired level of specificity. Generally, the specificity is at a level at which the binding partner binds preferentially to the analyte of interest rather than other compounds. Its affinity for the analyte of interest may be at least 2-fold, at least 5-fold, at least 10-fold, or more than its affinity for another compound. Binding patterns with the greatest differential affinity are preferred in most embodiments. The binding partners can be of any nature including but not limited to nucleic acid (e.g., aptamers), peptide, carbohydrate, lipid, and the like. A common form of binding partner is an antibody or an antigen-binding antibody fragment. Antibodies include IgG, IgA, IgM, IgE, IgD as well as antibody variants such as single chain antibodies. Antibody fragments contain an antigen-binding site and thus include but are not limited to Fab and F(ab)$_2$ fragments. A nucleic acid based binding partner such as an oligonucleotide can be used to recognize and bind DNA or RNA based analytes. The nucleic acid based binding partner can be DNA, RNA, LNA or PNA, although it is not so limited. It can also be a combination of one or more of these elements and/or can comprise other nucleic acid mimics.

Binding partners can be primary or secondary. Primary binding partners are those bound to the polymer. Secondary binding partners are those that bind to an analyte that is already bound to the primary binding partner. Preferably, the primary and secondary binding partners bind to different regions on an analyte, unless such sites are repeatedly present on the analyte. In other words, binding of either the primary or secondary binding partners should not effectively compete with or interfere with the binding of the other to the analyte. If used, generally only the secondary analyte-specific binding partners needs to be detectably labeled, although both binding partners may be labeled. Preferably, every labeled binding partner has multiple labels conjugated thereto in order in increase signal.

It is to be understood that in some embodiments the analyte is itself detectable and there is therefore no need for a secondary binding partner.

The timing of addition of the secondary binding partner to the sample can vary. For example, it may be added prior to, simultaneously with, or following addition of the polymer.

An analyte as used herein is a molecule or compound being detected, quantitated or analyzed according to the invention. Analytes can be any molecule for which a binding partner is available. In its broadest sense, the analytes can be detected using virtually any molecular recognition system, such as but not limited to antibodies, aptamers, carbohydrates, etc. The analytes can be organic or inorganic in nature, and in important embodiments, they include proteins, peptides, toxins such as microbial toxins, nucleic acids such as oligonucleotides, pathogens such as bacteria, viruses, fungi, parasites, mycobacteria, and the like. Although the analytes to be detected are not size restricted, those that are equal to or less than 500 nm are preferred in some embodiments.

The invention can be applied to the detection and optionally identification and/or quantification of any analyte, but most preferably rare analytes which would otherwise be costly to detect. One example of one such analyte is a biohazardous or biowarfare agent. These agents can be biological or chemical in nature. Biological biowarfare agents can be classified broadly as pathogens (including spores thereof) or toxins. As used herein, a pathogen (including a spore thereof) is an agent capable of entering a subject such as a human and infecting that subject. Examples of pathogens include infectious agents such bacteria, viruses, fungi, parasites, mycobacteria and the like. Prions may also be considered pathogens to the extent they are thought to be the transmitting agent for CJD and like diseases. As used herein, a toxin is a pathogen-derived agent that causes disease and often death in a subject without also causing an infection. It derives from pathogens and so may be harvested from such pathogens. Alternatively, it may be synthesized apart from pathogen sources. Biologicals may be weaponized (i.e., aerosolized) for maximum spread. Examples of biowarfare agents include those listed and categorized by the CDC.

CDC Category A agents include *Bacillus anthracis* (otherwise known as anthrax), *Clostridium botulinum* and its toxin (causative agent for botulism), *Yersinia pestis* (causative agent for the plague), variola major (causative agent for small pox), *Francisella tularensis* (causative agent for tularemia), and viral hemorrhagic fever causing agents such as filoviruses Ebola and Marburg and arenaviruses such as Lassa, Machupo and Junin.

CDC Category B agents include Brucellosis (*Brucella* species), epsilon toxin of *Clostridium perfringens*, food safety threats such as *Salmonella* species, *E. coli* and *Shigella*, Glanders (*Burkholderia mallei*), Melioidosis (*Burkholderia pseudomallei*), Psittacosis (*Chlamydia psittaci*), Q fever (*Coxiella burnetii*), ricin toxin (from *Ricinus communis*—castor beans), Staphylococcal enterotoxin B, Typhus fever (*Rickettsia prowazekii*), viral encephalitis (alphaviruses, e.g., Venezuelan equine encephalitis, eastern equine encephalitis, western equine encephalitis), and water safety threats such as e.g., *Vibrio cholerae, Cryptosporidium parvum*.

CDC Category C agents include emerging infectious diseases such as Nipah virus and *hantavirus*.

Other pathogens that can be detected using the methods of the invention include *N. gonorrhea, H. pylori, Staphylococcus* spp., *Streptococcus* spp. such as *Streptococcus pneumoniae*, Syphilis; viruses such as SARS virus, Hepatitis A, B and C viruses, Herpes virus, HIV, West Nile virus, Influenza A virus, *poliovirus, rhinovirus*; and parasites such as *Giardia*.

Examples of toxins include abrin, ricin and strychnine. Further examples of toxins include toxins produced by *Corynebacterium diphtheriae* (diphtheria), *Bordetella pertussis* (whooping cough), *Vibrio cholerae* (cholera), *Bacillus anthracis* (anthrax), *Clostridium botulinum* (botulism), *Clostridium tetani* (tetanus), and enterohemorrhagic *Escherichia coli* (bloody diarrhea and hemolytic uremic syndrome), *Staphylococcus aureus* alpha toxin, Shiga toxin (ST), cytotoxic necrotizing factor type 1 (CNF 1), *E. coli* heat-stable toxin (ST), botulinum, tetanus neurotoxins, *S. aureus* toxic shock syndrome toxin (TSST), *Aeromonas hydrophila* aerolysin, *Clostridium perfringens* perfringolysin O, *E. coli* hemolysin, *Listeria monocytogenes* listeriolysin O, *Streptococcus pneumoniae* pneumolysin, *Streptococcus pyogenes* streptolysine O, *Pseudomonas aeruginosa* exotoxin A, *E. coli* DNF, *E. coli* LT, *E. coli* CLDT, *E. coli* EAST, *Bacillus anthracis* edema factor, *Bordetella pertussis* dermonecrotic toxin, *Clostridium botulinum* C2 toxin, *C. botulinum* C3 toxin, *Clostridium difficile* toxin A, and *C. difficile* toxin B.

Further examples of bacteria that can be used as biohazards include *Pseudomonas* spp., *Clostridium difficile, Legionella* spp., *Pneumococcus* spp., *Haemophilus* spp. (e.g., *Haemophilus influenzae*), *Klebsiella* spp., *Enterobacter* spp., *Citrobacter* spp., *Neisseria* spp. (e.g., *N. meningitidis*), *Shigella* spp., *Salmonella* spp., *Listeria* spp. (e.g., *L. monocytogenes*), *Pasteurella* spp. (e.g., *Pasteurella multocida*), *Streptobacillus* spp., *Spirillum* spp., *Treponema* spp. (e.g., *Treponema pallidum*), *Actinomyces* spp. (e.g., *Actinomyces israelii*), *Borrelia* spp., *Corynebacterium* spp., *Nocardia* spp., *Gardnerella* spp. (e.g., *Gardnerella vaginalis*), *Campylobacter* spp., *Spirochaeta* spp., *Proteus* spp., and *Bacteriodes* spp.

Further examples of viruses that can be used as biohazards include Herpes simplex virus 1 and 2 (including encephalitis, neonatal and genital forms), human papilloma virus, *cytomegalovirus*, Epstein Barr virus, *rotavirus, adenovirus*, influenza virus, respiratory syncytial virus, varicella-zoster virus, small pox and monkey pox.

Further examples of fungi that can be used as biohazards include candidiasis, ringworm, histoplasmosis, blastomycosis, paracoccidioidomycosis, crytococcosis, aspergillosis, chromomycosis, mycetoma, pseudallescheriasis, and tinea versicolor.

Further examples of parasites that can be used as biohazards include both protozoa and nematodes such as amebiasis, *Trypanosoma cruzi*, Fascioliasis (e.g., *Facioloa hepatica*), Leishmaniasis, *Plasmodium* (e.g., *P. falciparum, P. knowlesi, P. malariae*) Onchocerciasis, Paragonimiasis, *Trypanosoma brucei, Pneumocystis* (e.g., *Pneumocystis carinii*), *Trichomonas vaginalis, Taenia, Hymenolepsis* (e.g., *Hymenolepsis nana*), *Echinococcus*, Schistosomiasis (e.g., *Schistosoma mansoni*), neurocysticercosis, *Necator americanus*, and *Trichuris trichuria*.

Further examples of pathogens that can be used as biohazards include: *Chlamydia, M. tuberculosis* and M. leprosy, and Rickettsiae.

Examples of chemicals that can be detected include arsenic, arsine, benzene, blister agents/vesicants, blood agents, bromine, borombenzylcyanide, chlorine, choking/lung/pulmonary agents, cyanide, distilled mustard, fentanyls and other opioids, mercury, mustard gas, nerve agents, nitrogen mustard, organic solvents, paraquat, phosgene, phosphine, sarin, sesqui mustard, stibine, sulfur mustard, warfarin, tabun, and the like.

The foregoing lists of infections are not intended to be exhaustive but rather exemplary.

The number of detectable analytes is usually not limited by number of different signals (or labels) but more often by the number of resolvable sites in the polymer. For example, all of the secondary analyte-specific binding partners can be labeled with the same detectable label (e.g., all labeled with a FITC fluorophore) since this label can be used simply to indicate the presence of an analyte and the barcode is used to determine the identity of the analyte. It is the combination of a particular barcode (e.g., barcode 1) with a fluorescein signal that indicates the presence of a particular analyte (e.g., analyte 1). The combination of another barcode (e.g., barcode 2) with a fluorescein signal indicates the presence of another particular analyte (e.g., analyte 2). While it may be desirable to use different labels on secondary analyte-specific binding partners, e.g., when analyte concentration is to be determined, this is not necessary.

The methods can detect a plurality of analytes using a plurality of different analyte-specific binding partners and a plurality of polymers. A plurality as used herein is more than one and can be at least 3, at least 4, at least 5, at least 10, at least 25, at least 50, at least 75, at least 100, at least 200, at least 500, or more.

The sample to be tested for analyte presence and/or amount can be derived from virtually any source and will depend primarily on the analyte being detected. The sample may be a biological sample from a subject such as a bodily fluid or tissue. The term tissue as used herein refers to both localized and disseminated cell populations including, but not limited, to brain, heart, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea and lung. Biological fluids include saliva, sperm, serum, plasma, blood, lymph and urine, but are not so limited. Both invasive and non-invasive techniques can be used to obtain such samples and these are known to those of ordinary skill in the art.

Alternatively, the sample may be an environmental sample such as an air sample or a water sample. In this latter embodiment, the sample may be checked for, for example, chemical or biological warfare agents such as those recited herein. If the sample is an air sample, it will generally require dissolution in a liquid base such as a buffered solution. This is usually also the case with solid samples.

The analyte being detected can dictate whether the sample needs to be further manipulated prior to analysis. In some embodiments, it may be necessary to disrupt larger analytes such as pathogens prior to contact with the binding partner. Disruption can be mechanical, including acoustic disruption (e.g., ultrasound based disruption), and may be carried out to varying degrees. For example, a sample may be disrupted to the point of rupturing cell walls and/or cell membranes and releasing cell wall fragments, intracellular organelles, proteins, lipids, and/or genomic DNA, all of which may be analytes.

Depending on the expected concentration of the analyte being detected, the sample may be diluted or concentrated prior to analysis. Dilution will generally involve mixing of the sample with a larger volume of solution. Concentration can be accomplished in a number of ways known in the art including but not limited to centrifugation, filtering, and the like. Concentration may also be accomplished using flow directed concentration methods.

The invention can be used to determine the concentration or absolute amount of an analyte in a sample. The concentration or amount of the analyte is determined by measuring the amount of signal from an analyte bound to a polymer. This signal can be from an intrinsically detectable analyte or from a detectably labeled secondary analyte-specific binding partner. As will be understood by those of ordinary skill, each polymer must be conjugated to enough analyte-specific binding partners to enable a wide range of analyte concentrations to be detected. In other words, the number of analyte-specific binding partners must be greater than the number of analytes in the sample so as not to be saturated. If the analyte concentration in the test solution is very high, the test solution can be diluted in order to quantitate analyte concentration accurately. The signal level can be compared to a standard calibration curve that is prepared prior to or at the same time as the test solution is analyzed. The standard calibration curve is a plot of signal intensity (y-axis) as a function of analyte concentration (x-axis). Those of ordinary skill will be familiar with the generation of such curves.

The various embodiments of the invention described herein make specific reference to a polymer that is DNA and primary and second analyte-specific binding partners that are antibodies. It is to be understood however that these descriptions are intended as illustrative only and are not meant to limit the scope of the invention. Thus, any polymer can be used in the methods of the invention. Similarly, any analyte-specific binding partner can be used as either or both the first and second analyte-specific binding partners.

Thus, in one illustrative embodiment, the polymer is a DNA having a particular sequence unique to that DNA and referred to herein as the barcode. The DNA has bound to it antibodies or antibody fragments that recognize and bind to the analyte (i.e., analyte-specific antibodies or antibody fragments). The DNA is incubated with a sample taken for example from a larger test solution (i.e., an aliquot of a test solution). The incubation time and conditions are dictated by the particular analyte and the binding affinity of the antibody. One of ordinary skill in the art is capable of determining these parameters. The DNA/analyte complex is then exposed to a soluble secondary analyte-specific antibody that is itself detectably labeled, for example with a fluorophore or a radioisotope. The type of detection system to be used or available will dictate the type of detectable labels that are suitable. The presence of an analyte in the sample (and thus, the test solution) is indicated by the presence of an analyte-specific detectable label on the DNA. The identity of the analyte is dictated by the sequence (or barcode) of the DNA.

The DNA can be labeled prior to, during or following analyte binding. It can be labeled using labeled nucleotides that are incorporated during its synthesis, or by binding to it one or more labeled probes, although as discussed herein such labeling is not limited in this regard. The DNA barcode may be comprised of one or more spatially separated labels.

In another illustrative example, a polymer such as a DNA is bound to a detectable probe such as a fluorescent sequence-specific probe that recognizes a particular sequence motif in the DNA and binds to it. The molecule is interrogated and the location of binding of the probe is determined. FIG. 1 illustrates the DNA (horizontal line) and the particular bound probes (vertical lines). Each DNA may have one or more bound probes. The binding pattern of the probes along the DNA can be used to identify the DNA and consequently its analyte binding specificity.

Figure 1B:
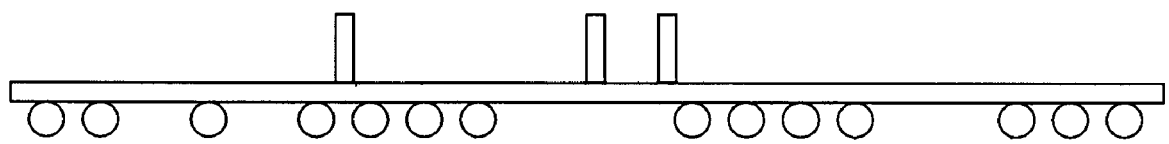
Figure 1C:
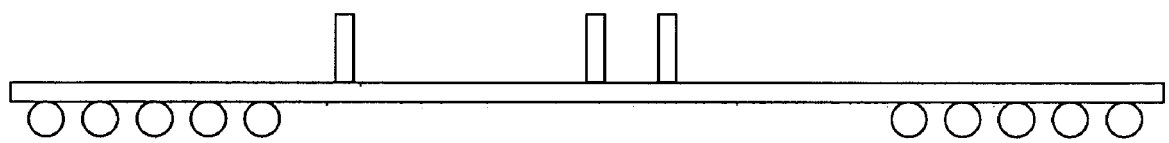

The polymer also comprises analyte-specific binding sites imparted by analyte-specific binding partners, which are indicated by circles in FIG. 1. These sites can be located in any conformation or sequence along the length of the DNA. For example, these sites can be evenly distributed along the DNA molecule (FIG. 1A), grouped in clusters (FIG. 1B), concentrated in termini-adjacent regions (FIG. 1C), or randomly distributed. It is to be understood that the placement of the primary analyte-specific binding partners on the polymer may be different between polymers that nevertheless have identical analyte binding specificity, provided preferably that the analyte-specific binding partners are not also being used as the basis of the barcode.

Figure 2:
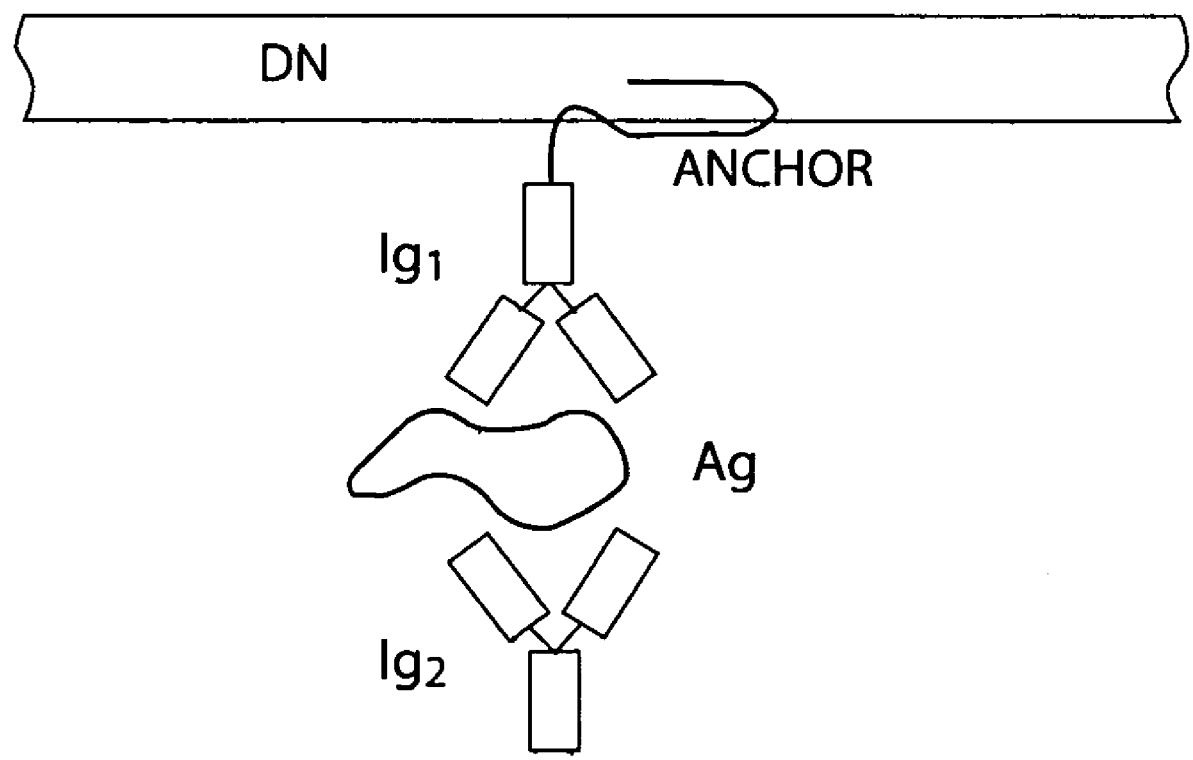
FIG. 2 illustrates the conjugation of a primary analyte-specific binding partner that is an antibody to a polymer that is a nucleic acid. The analyte is referred to as an antigen (Ag). The analyte is further recognized by a secondary analyte-specific binding partner that is also an antibody. The primary and secondary analyte-specific binding partners may both be labeled, although most embodiments minimally require labeling of the latter. Alternatively, if the analyte is itself directly detectable (e.g., it is inherently fluorescent), then there is no need for the secondary analyte-specific binding partner.

An example of the analyte-specific binding site is presented in FIG. 2. In this example, a monoclonal antibody (e.g., $Ig_1$) is anchored to a DNA. This can be done either covalently (e.g., using one of many possible techniques known to those of ordinary skill in the art) or non-covalently (e.g., through bisPNA, biotin-streptavidin complex, etc.). Once the antibody encounters its corresponding antigen (Ag), it binds to it. The analyte can also bind another antibody $Ig_2$ specific for a different epitope in its structure (thereby forming a so-called sandwich-immunoassay). The secondary antibody is preferably labeled with a detectable label such as a fluorophore.

Figure 3A:
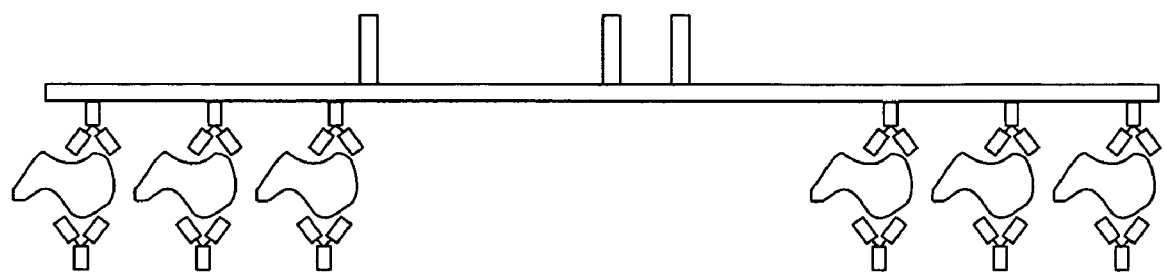
FIG. 3 illustrates binding of two different polymers (i.e., polymers having different bar codes indicated by vertical lines) to different analytes (indicated by differently shaped objects in panel A and panel B). The location of the primary analyte-specific binding partners can differ between polymers recognizing the same analyte.
Figure 3B:
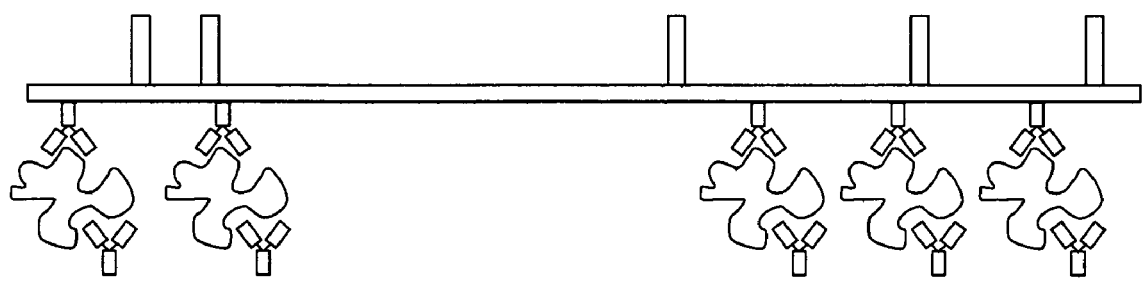
Figure 4:
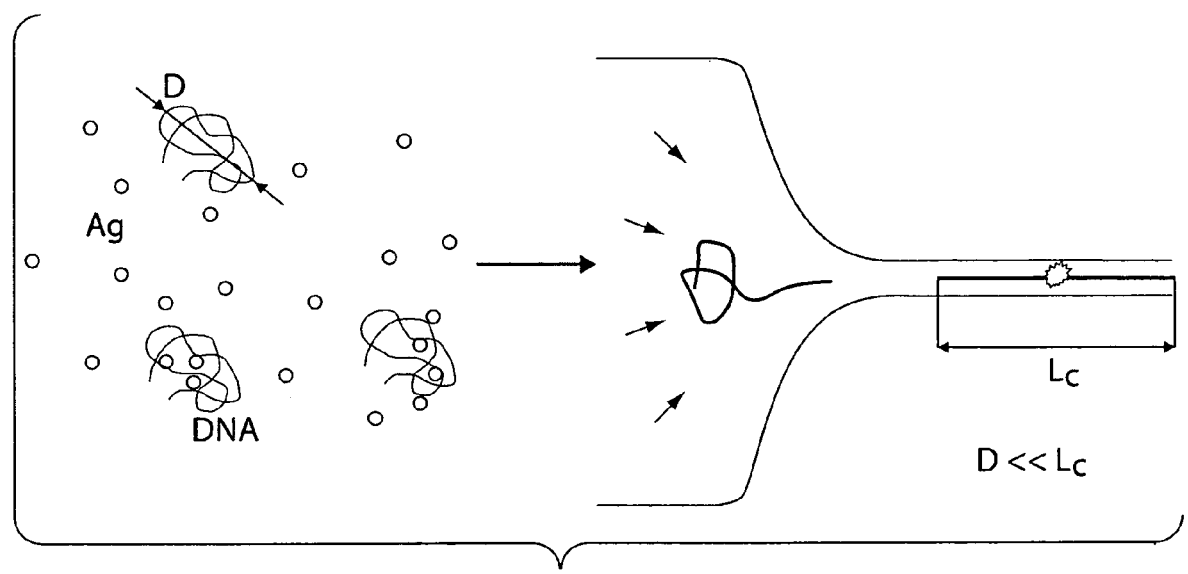
FIG. 4 illustrates a polymer in both a compact form (prior to entering an interrogation zone) and in an elongated (or stretched) form (while in the interrogation zone).

Preferably, DNAs having different sequences (and thus different barcodes) have different primary antibodies bound thereto (compare FIGS. 3A and 3B). Prior to analysis using one of the systems described herein, a solution containing different analytes is incubated with DNAs having analyte-specific antibodies attached thereto (FIG. 4, left). The solution may also include secondary antibodies. Alternatively, they may be added later in time. The secondary antibodies preferably are conjugated to detectable labels (e.g., fluorophores). During the incubation period, the first and second analyte-specific binding partners bind to the analyte either simultaneously or in succession.

Figure 5A:
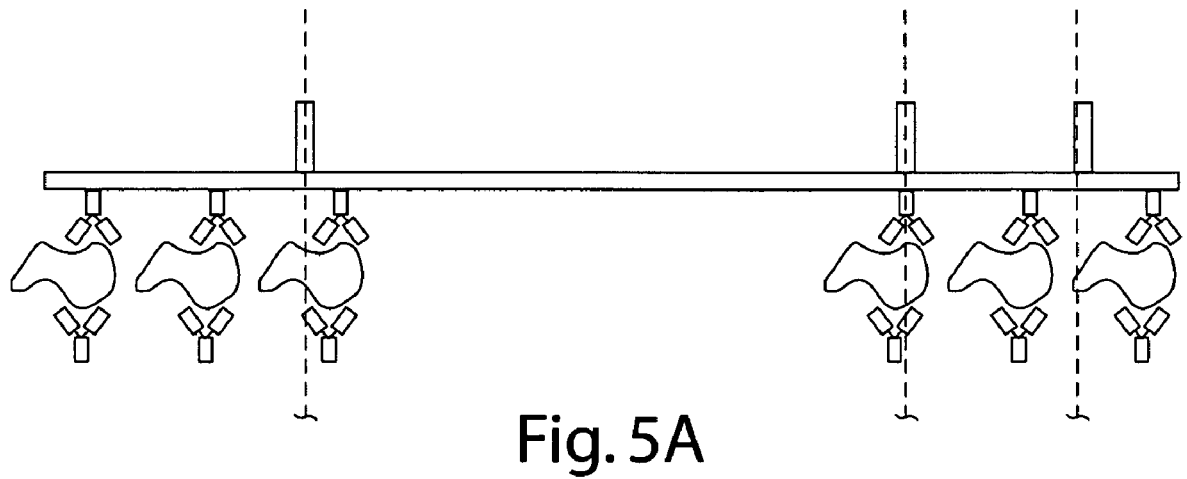
FIGS. 5A and 5B each illustrates the use of one or more primary analyte-specific binding partners as the basis of the bar code.
Figure 5B:
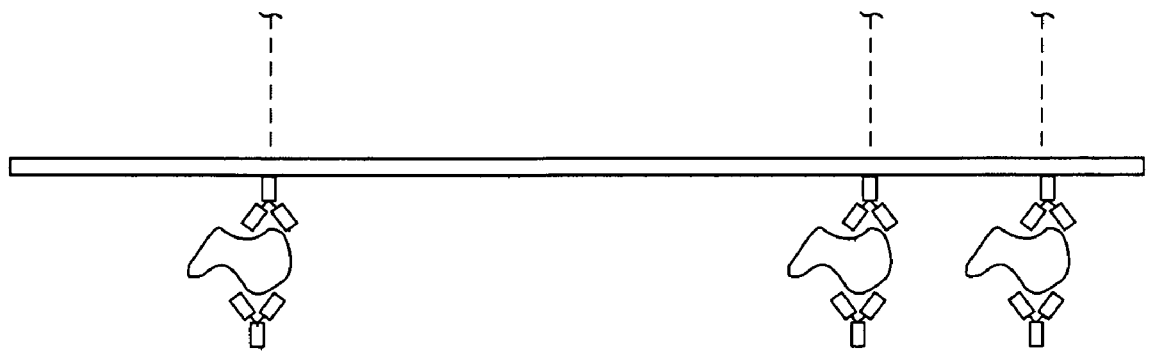

In another embodiment, the analyte-specific binding partners are bound at specific defined locations rather than being randomly distributed across the polymer length (FIG. 5). In this example, primary antibodies Ig are conjugated with green fluorophores and their fluorescence is used as the basis of the barcode. In this example, the analyte-specific binding partners form the barcode and bind analyte.

The sample may be analyzed using a single polymer analysis system such as but not limited to GeneEngine™. Movement of the sample in a microfluidic chamber of GeneEngine™ is shown in FIG. 4. When placed in a moving fluid, DNA is stretched in the microfluidic chip and translocated into an interrogation channel. Once in the interrogation channel, stretched DNA passes through the interrogation zone (e.g., a spot of excitation light). In some embodiments, the spot diameter is about 0.5 µm, and therefore much smaller than the stretched DNA length which is about 34 µm for 100 kb DNA.

In one embodiment, the GeneEngine™ platform is used with focusing flow design ([3], and e.g., Luminex® LX-100 flow cytometer). This arrangement provides interrogation of all polymers, improves polymer stretching, and moves the sample through the center of the excitation beam for more efficient detection. This arrangement therefore increases signal to noise (S/N) ratio and minimizes dispersion of excitation power.

Using such flow configurations, it is also possible to concentrate and/or redirect polymers of interest, such as polymers having an analyte of interest bound thereto. In a flow system, this is easily accomplished by redirecting flow into a collection vessel. The collected polymer can then be manipulated, possibly to dissociate the analyte from its respective binding partner(s). The analyte whether in free or bound form can then be analyzed in greater detail. For example, if the analyte is a nucleic acid, it may be analyzed via PCR.

Figure 6:
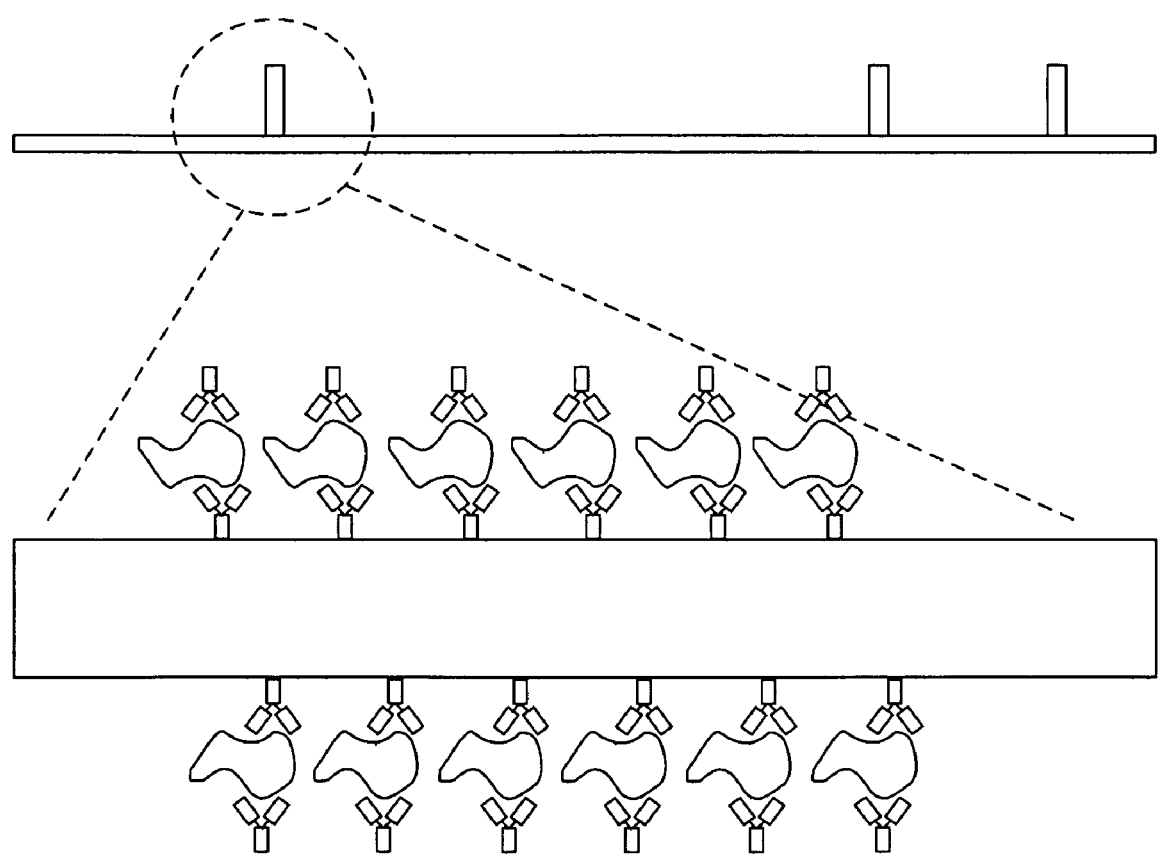
FIG. 6 illustrates one or more analyte-specific binding partners, in the form of primary antibodies Ig, bound at a specific mapping site on the polymer.

In another embodiment, one or more primary antibodies Ig are bound at a specific site (FIG. 6). The number of antibodies bound should not interfere with barcode formation or detection. For example, individual sequence sites contributing to a barcode should not be located so close to each other as to not be detectable as separate sites (i.e., the distance between these sites should be greater than the minimal resolution distance). Reference can be made to published U.S. Patent Application Publication No. 2003-0059822 A1 and/or published PCT Application No. WO 03/025540 for a discussion of minimal resolution distances. Additionally, the length of each site contributing to a barcode should not exceed the resolution limit of the detection system. For example, if the interrogation is performed at a 1 kilobase resolution (e.g., the resolution limit for a given analysis), then the length of each site should not exceed 0.34 µm (i.e., the length of 1 kb B-form DNA [2]). The length of the sequence site may be defined for example as the length of a given nucleotide sequence bound by a probe or as the length of the polymer region bound by a primary analyte-specific binding partner. In the preceding example, a 1 kb B-form DNA molecule can accommodate at least 30 antibodies on sufficiently long tethers. In this arrangement, strong fluorescence signals are attainable.

The term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" are used interchangeably and refer to oligoribonucleotides as well as oligodeoxyribonucleotides. The terms shall also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. Nucleic acids can be obtained from natural sources, or can be synthesized using a nucleic acid synthesizer.

As used herein with respect to linked units of a polymer including a nucleic acid, "linked" or "linkage" means two entities bound to one another by any physicochemical means. Any linkage known to those of ordinary skill in the art, covalent or non-covalent, is embraced. Natural linkages, which are those ordinarily found in nature connecting for example the individual units of a particular nucleic acid, are most common. Natural linkages include, for instance, amide, ester and thioester linkages. The individual units of a nucleic acid analyzed by the methods of the invention may be linked, however, by synthetic or modified linkages. Nucleic acids where the units are linked by covalent bonds will be most common but those that include hydrogen bonded units are also embraced by the invention. It is to be understood that all possibilities regarding nucleic acids apply equally to nucleic acid targets and nucleic acid probes.

In some embodiments, the invention embraces nucleic acid derivatives as polymers and/or probes. As used herein, a "nucleic acid derivative" is a non-naturally occurring nucleic acid or a unit thereof. Nucleic acid derivatives may contain non-naturally occurring elements such as non-naturally occurring nucleotides and non-naturally occurring backbone linkages. These include substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. Other such modifications are well known to those of skill in the art.

The nucleic acid derivatives may also encompass substitutions or modifications, such as in the bases and/or sugars. For example, they include nucleic acids having backbone sugars which are covalently attached to low molecular weight organic groups other than a hydroxyl group at the 3' position and other than a phosphate group at the 5' position. Thus, modified nucleic acids may include a 2'-O-alkylated ribose group. In addition, modified nucleic acids may include sugars such as arabinose instead of ribose.

The nucleic acids may be heterogeneous in backbone composition thereby containing any possible combination of nucleic acid units linked together such as peptide nucleic acids (which have amino acid linkages with nucleic acid bases, and which are discussed in greater detail herein). In some embodiments, the nucleic acids are homogeneous in backbone composition.

The polymers and probes if comprising nucleic acid components can be stabilized in part by the use of backbone modifications. The invention intends to embrace, in addition to the peptide and locked nucleic acids discussed herein, the use of the other backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, the polymer or probe is a nucleic acid that is a peptide nucleic acid (PNA), a bisPNA clamp, a pseudocomplementary PNA, a locked nucleic acid (LNA), DNA, RNA, or co-nucleic acids of the above such as DNA-LNA co-nucleic acids. In some instances, the nucleic acid target can also be comprised of any of these elements.

PNAs are DNA analogs having their phosphate backbone replaced with 2-aminoethyl glycine residues linked to nucleotide bases through glycine amino nitrogen and methylenecarbonyl linkers. PNAs can bind to both DNA and RNA targets by Watson-Crick base pairing, and in so doing form stronger hybrids than would be possible with DNA or RNA based probes.

PNAs are synthesized from monomers connected by a peptide bond (Nielsen, P. E. et al. *Peptide Nucleic Acids, Protocols and Applications*, Norfolk: Horizon Scientific Press, p. 1-19 (1999)). They can be built with standard solid phase peptide synthesis technology. PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNAs.

PNA has a charge-neutral backbone, and this attribute leads to fast hybridization rates of PNA to DNA (Nielsen, P. E. et al. *Peptide Nucleic Acids, Protocols and Applications*, Norfolk: Horizon Scientific Press, p. 1-19 (1999)). The hybridization rate can be further increased by introducing positive charges in the PNA structure, such as in the PNA backbone or by addition of amino acids with positively charged side chains (e.g., lysines). PNA can form a stable hybrid with DNA molecule. The stability of such a hybrid is essentially independent of the ionic strength of its environment (Orum, H. et al., *BioTechniques* 19(3): 472-480 (1995)), most probably due to the uncharged nature of PNAs. This provides PNAs with the versatility of being used in vivo or in vitro. However, the rate of hybridization of PNAs that include positive charges is dependent on ionic strength, and thus is lower in the presence of salt.

Several types of PNA designs exist, and these include single strand PNA (ssPNA), bisPNA and pseudocomplementary PNA (pcPNA).

The structure of PNA/DNA complex depends on the particular PNA and its sequence. Single stranded PNA (ssPNA) binds to single stranded DNA (ssDNA) preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with double stranded DNA (dsDNA) (Wittung, P. et al., *Biochemistry* 36: 7973 (1997)).

Single strand PNA is the simplest of the PNA molecules. This PNA form interacts with nucleic acids to form a hybrid duplex via Watson-Crick base pairing. The duplex has different spatial structure and higher stability than dsDNA (Nielsen, P. E. et al. *Peptide Nucleic Acids, Protocols and Applications*, Norfolk: Horizon Scientific Press, p. 1-19 (1999)). However, when different concentration ratios are used and/or in presence of complimentary DNA strand, PNA/DNA/PNA or PNA/DNA/DNA triplexes can also be formed (Wittung, P. et al., *Biochemistry* 36: 7973 (1997)). The formation of duplexes or triplexes additionally depends upon the sequence of the PNA. Thymine-rich homopyrimidine ssPNA forms PNA/DNA/PNA triplexes with dsDNA targets where one PNA strand is involved in Watson-Crick antiparallel pairing and the other is involved in parallel Hoogsteen pairing. Cytosine-rich homopyrimidine ssPNA preferably binds through Hoogsteen pairing to dsDNA forming a PNA/DNA/DNA triplex. If the ssPNA sequence is mixed, it invades the dsDNA target, displaces the DNA strand, and forms a Watson-Crick duplex. Polypurine ssPNA also forms triplex PNA/DNA/PNA with reversed Hoogsteen pairing.

BisPNA includes two strands connected with a flexible linker. One strand is designed to hybridize with DNA by a classic Watson-Crick pairing, and the second is designed to hybridize with a Hoogsteen pairing. The target sequence can be short (e.g., 8 bp), but the bisPNA/DNA complex is still stable as it forms a hybrid with twice as many (e.g., a 16 bp) base pairings overall. The bisPNA structure further increases specificity of their binding. As an example, binding to an 8 bp site with a probe having a single base mismatch results in a total of 14 bp rather than 16 bp.

Preferably, bisPNAs have homopyrimidine sequences, and even more preferably, cytosines are protonated to form a Hoogsteen pair to a guanosine. Therefore, bisPNA with thymines and cytosines is capable of hybridization to DNA only at pH below 6.5. The first restriction—homopyrimidine sequence only—is inherent to the mode of bisPNA binding. Pseudoisocytosine (J) can be used in the Hoogsteen strand instead of cytosine to allow its hybridization through a broad pH range (Kuhn, H., *J. Mol. Biol.* 286: 1337-1345 1999)).

BisPNAs have multiple modes of binding to nucleic acids (Hansen, G. I. et al., *J. Mol. Biol.* 307(1): 67-74 (2001)). One isomer includes two bisPNA molecules instead of one. It is formed at higher bisPNA concentration and has a tendency to rearrange into the complex with a single bisPNA molecule. Other isomers differ in positioning of the linker around the target DNA strands. All the identified isomers still bind to the same binding site/target.

Pseudocomplementary PNA (pcPNA) (Izvolsky, K. I. et al., *Biochemistry* 10908-10913 (2000)) involves two single stranded PNAs added to dsDNA. One pcPNA strand is complementary to the target sequence, while the other is complementary to the displaced DNA strand. As the PNA/DNA duplex is more stable, the displaced DNA generally does not restore the dsDNA structure. The PNA/PNA duplex is more stable than the DNA/PNA duplex and the PNA components are self-complementary because they are designed against complementary DNA sequences. Hence, the added PNAs would rather hybridize to each other. To prevent the self-hybridization of pcPNA units, modified bases are used for their synthesis including 2,6-diamiopurine (D) instead of adenine and 2-thiouracil ($^SU$) instead of thymine. While D and $^SU$ are still capable of hybridization with T and A respectively, their self-hybridization is sterically prohibited.

Locked nucleic acid (LNA) molecules form hybrids with DNA, which are at least as stable as PNA/DNA hybrids (Braasch, D. A. et al., *Chem & Biol.* 8(1): 1-7(2001)). Therefore, LNA can be used just as PNA molecules would be. LNA binding efficiency can be increased in some embodiments by adding positive charges to it. LNAs have been reported to have increased binding affinity inherently.

Commercial nucleic acid synthesizers and standard phosphoramidite chemistry are used to make LNAs. Therefore, production of mixed LNA/DNA sequences is as simple as that of mixed PNA/peptide sequences. The stabilization effect of LNA monomers is not an additive effect. The monomer influences conformation of sugar rings of neighboring deoxynucleotides shifting them to more stable configurations (Nielsen, P. E. et al. *Peptide Nucleic Acids, Protocols and Applications*, Norfolk: Horizon Scientific Press, p. 1-19 (1999)). Also, lesser number of LNA residues in the sequence dramatically improves accuracy of the synthesis. Naturally, most of biochemical approaches for nucleic acid conjugations are applicable to LNA/DNA constructs.

Other backbone modifications, particularly those relating to PNAs, include peptide and amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), amino acids such as lysine (particularly useful if positive charges are desired in the PNA), and the like. Various PNA modifications are known and probes incorporating such modifications are commercially available from sources such as Boston Probes, Inc.

As stated herein, one way of generating a labeling pattern or a barcode is to use one or more sequence-specific probes. "Sequence-specific" when used in the context of a probe for a nucleic acid polymer means that the probe recognizes a particular linear (or quasi-linear) arrangement of nucleotides or derivatives thereof. In preferred embodiments, the probe is itself composed of nucleic acid elements such as DNA, RNA, PNA and LNA elements and combinations thereof (as discussed below). In preferred embodiments, the linear arrangement includes contiguous nucleotides or derivatives thereof that each binds to a corresponding complementary nucleotide in the probe. In some embodiments, however, the sequence may not be contiguous as there may be one, two, or more nucleotides that do not have corresponding complementary residues on the probe.

Any molecule that is capable of recognizing a polymer such as a nucleic acid with structural or sequence specificity can be used as a sequence-specific probe. In most instances, such probes will form at least a Watson-Crick bond with the nucleic acid polymer. In other instances, the nucleic acid probe can form a Hoogsteen bond with the nucleic acid polymer, thereby forming a triplex. A nucleic acid probe that binds by Hoogsteen binding enters the major groove of a nucleic acid polymer and hybridizes with the bases located there. Examples of these latter probes include molecules that recognize and bind to the minor and major grooves of nucleic acids (e.g., some forms of antibiotics). In some embodiments, the nucleic acid probes can form both Watson-Crick and Hoogsteen bonds with the nucleic acid polymer. BisPNA probes, for instance, are capable of both Watson-Crick and Hoogsteen binding to a nucleic acid.

The length of probe can also determine the specificity of binding. The energetic cost of a single mismatch between the probe and the nucleic acid polymer is relatively higher for shorter sequences than for longer ones. Therefore, hybridization of smaller nucleic acid probes is more specific than is hybridization of longer nucleic acid probes because the longer probes can embrace mismatches and still continue to bind to the polymer depending on the conditions. One potential limitation to the use of shorter probes however is their inherently lower stability at a given temperature and salt concentration. In order to avoid this latter limitation, bisPNA probes can be used to bind shorter sequences with sufficient hybrid stability.

Notwithstanding these provisos, the nucleic acid probes of the invention can be any length ranging from at least 4 nucleotides to in excess of 1000 nucleotides. In preferred embodiments, the probes are 5-100 nucleotides in length, more preferably between 5-25 nucleotides in length, and even more preferably 5-12 nucleotides in length. The length of the probe can be any length of nucleotides between and including the ranges listed herein, as if each and every length was explicitly recited herein. Thus, the length may be at least 5 nucleotides, at least 10 nucleotides, at least 15 nucleotides, at least 20 nucleotides, or at least 25 nucleotides, or more, in length. It should be understood that not all residues of the probe need hybridize to complementary residues in the nucleic acid target. For example, the probe may be 50 residues in length, yet only 25 of those residues hybridize to the nucleic acid target. Preferably, the residues that hybridize are contiguous with each other.

The probes are preferably single stranded, but they are not so limited. For example, when the probe is a bisPNA it can adopt a secondary structure with the nucleic acid polymer resulting in a triple helix conformation, with one region of the bisPNA clamp forming Hoogsteen bonds with the backbone of the polymer and another region of the bisPNA clamp forming Watson-Crick bonds with the nucleotide bases of the polymer.

The nucleic acid probe hybridizes to a complementary sequence within the nucleic acid polymer. The specificity of binding can be manipulated based on the hybridization conditions. For example, salt concentration and temperature can be modulated in order to vary the range of sequences recognized by the nucleic acid probes. Those of ordinary skill in the art will be able to determine optimum conditions for a desired specificity.

As stated herein, the polymer may be directly labeled. As an example, if the polymer is a nucleic acid, it may be labeled through the use of sequence-specific probes that bind to the polymer in a sequence-specific manner. The sequence-specific probes are labeled with a detectable label (e.g., a fluorophore or a radioisotope). The nucleic acid however can also be synthesized in a manner that incorporates fluorophores directly into the growing nucleic acid. For example, this latter labeling can be accomplished by chemical means or by the introduction of active amino or thiol groups into nucleic acids. (Proudnikov and Mirabekov, Nucleic Acid Research, 24: 4535-4532, 1996.) An extensive description of modification procedures that can be performed on a nucleic acid polymer can be found in Hermanson, G. T., Bioconjugate Techniques, Academic Press, Inc., San Diego, 1996, which is incorporated by reference herein.

There are several known methods of direct chemical labeling of DNA (Hermanson, 1996; Roget et al., 1989; Proudnikov and Mirabekov, 1996). One of the methods is based on the introduction of aldehyde groups by partial depurination of DNA. Fluorescent labels with an attached hydrazine group are efficiently coupled with the aldehyde groups and the hydrazine bonds are stabilized by reduction with sodium labeling efficiencies around 60%. The reaction of cytosine with bisulfite in the presence of an excess of an amine fluorophore leads to transamination at the N4 position (Hermanson, 1996). Reaction conditions such as pH, amine fluorophore concentration, and incubation time and temperature affect the yield of products formed. At high concentrations of the amine fluorophore (3M), transamination can approach 100% (Draper and Gold, 1980).

In addition to the above method, it is also possible to synthesize nucleic acids de novo (e.g., using automated nucleic acid synthesizers) using fluorescently labeled nucleotides. Such nucleotides are commercially available from suppliers such as Amersham Pharmacia Biotech, Molecular Probes, and New England Nuclear/Perkin Elmer.

Probes or analyte-specific binding partner may also be labeled, for example, using a detectable label. A detectable label is a moiety, the presence of which can be ascertained directly or indirectly. Generally, detection of the label involves the creation of a detectable signal such as for example an emission of energy. The label may be of a chemical, peptide or nucleic acid nature although it is not so limited. The nature of label used will depend on a variety of factors, including the nature of the analysis being conducted, the type of the energy source and detector used and the type of polymer, analyte, probe and primary and secondary analyte-specific binding partners. The label should be sterically and chemically compatible with the constituents to which it is bound.

The label can be detected directly for example by its ability to emit and/or absorb electromagnetic radiation of a particular wavelength. A label can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.). Generally the detectable label can be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl) aminonaphthalene-1-sulfonic acid (EDANS), 4-acetamido-4'-isothiocyanatostilbene-2, 2'disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4', 6-diaminidino-2-phenylindole (DAPI), 5',5''-diaminidino-2-phenylindole (DAPI), 5',5''-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl) aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives), a chemiluminescent molecule, a bioluminescent molecule, a chromogenic molecule, a radioisotope (e.g., $P^{32}$ or $H^3$, $^{14}C$, $^{125}I$ and $^{131}I$), an electron spin resonance molecule (such as for example nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described for example in U.S. Pat. No. 6,207,392 and commercially available from Quantum Dot Corporation and Evident Technologies), a colloidal metal, a colloid gold nanocrystal, a nuclear magnetic resonance molecule, and the like.

The detectable label can also be selected from the group consisting of indirectly detectable labels such as an enzyme (e.g., alkaline phosphatase, horseradish peroxidase, β-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, and the like. Antibody fragments include Fab, F(ab)$_2$, Fd and antibody fragments which include a CDR3 region.

In some embodiments, primary and secondary analyte-specific binding partners are conjugated with donor and acceptor fluorophores, respectively, that form a FRET (fluorescence resonance energy transfer) pair. In this case, a blue laser light is used to excite fluorescence of donor fluorophores. A portion of the energy absorbed by the donors can be transferred to acceptor fluorophores if they are spatially close enough to the donor molecules (i.e., the distance between them must approximate or be less than the Forster radius or the energy transfer radius). Once the acceptor fluorophore absorbs the energy, it in turn fluoresces in its characteristic emission wavelength. Since energy transfer is possible only when the acceptor and donor are located in close proximity, acceptor fluorescence is unlikely if the secondary analyte-specific binding partner is not bound to the analyte which is in turn bound to the primary analyte-specific binding partner. Acceptor fluorescence therefore can be used to determine presence and optionally concentration of analyte.

In some instances, a portion of donor fluorescence is detectable (i.e., it is not all transferred to the acceptor fluorophore) and thus can be used as the basis of the polymer barcode. This can eliminate the need for separate polymer labeling in order to generate the barcode. However, as described herein, in these embodiments, the first analyte-specific binding partner must be conjugated to the polymer in a known and thus non-random manner.

FRET alone generally requires only one excitation source (and thus wavelength) and sometimes only one detector. The detector may be set to either the emission spectrum of the donor or acceptor fluorophore. It is set to the donor fluorophore emission spectrum if FRET is detected by quenching of donor fluorescence. Alternatively, it is set to the acceptor fluorophore emission spectrum if FRET is detected by acceptor fluorophore emission. In some embodiments, FRET emissions of both donor and acceptor fluorophores can be detected. In still other embodiments, the donor is excited with polarized light and polarization of both emission spectra is detected.

FRET requires the use of a FRET fluorophore pair. FRET fluorophore pairs are two fluorophores that are capable of undergoing FRET to produce or eliminate a detectable signal when positioned in proximity to one another. Examples of donors include Alexa 488, Alexa 546, BODIPY 493, Oyster 556, Fluor (FAM), Cy3 and TMR (Tamra). Examples of acceptors include Cy5, Alexa 594, Alexa 647 and Oyster 656. Cy5 can work as a donor with Cy3, TMR or Alexa 546, as an example. FRET should be possible with any fluorophore pair having fluorescence maxima spaced at 50-100 nm from each other.

In a preferred embodiment, every analyte-specific binding partner that is to be directly detected is conjugated with many of the same detectable label (e.g., fluorophores). Multiple labels result in stronger fluorescence signals, greater signal to noise ratios, and thus better detection.

The polymer may be labeled in a sequence non-specific manner in addition to the barcode labeling discussed herein. For example, if the polymer is a nucleic acid such as DNA, then its backbone may be stained with a backbone label. Examples of backbone stains that label nucleic acids in a sequence non-specific manner include intercalating dyes such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc.

Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, Oli-Green, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25

(green), SYTO-81, -80, -82, -83, -84, -85 (orange), SYTO-64, -17, -59, -61, -62, -60, -63 (red).

In instances in which the nucleic acid polymer is stained with a non-specific backbone stain, the detection system should be capable of detecting and distinguishing between three distinct signals (i.e., one for the backbone, one for the sequence-specific sites that make up the barcode or labeling pattern, and one for the analyte or the secondary analyte-specific binding partner). Such a system should then be equipped for three color detection and three color excitation. If the FRET configuration is used as described herein, then the number of excitation lasers and/or detectors may be reduced.

As an example, in one embodiment, three different lasers are used for excitation at the following wavelengths: 488 nm (blue), 532 nm (green), and 633 nm (red). These lasers excite fluorescence of Alexa 488, TMR (tetramethylrhodamine), and TOTO-3 fluorophores, respectively. Fluorescence from all these fluorophores can be detected independently. As an example of fluorescence strategy, the sequence-specific probes or the DNA itself may be labeled with Alexa 488 fluorophores, the secondary antibodies may be labeled with TMR, and the DNA backbone may be labeled with TOTO-3. TOTO-3 is an intercalating dye that non-specifically stains DNA in a length-proportional manner. In this configuration, Alexa 488 fluorescence is used to determine the barcode or labeling pattern, TMR fluorescence bound to the DNA is indicative of analyte presence in the test solution (and thus bound to the DNA), and TOTO-3 fluorescence provides context for the barcode signal by labeling part of or the entire length of the DNA polymer, in some instances thereby allowing fine tuning of the barcode. TMR fluorescence can also be used to quantitate analyte concentration in the solution, as discussed herein. Another suitable set of fluorophores that can be used is the combination of POPO-1, TMR and Alexa 647 (or Cy5) which are excited by 442, 532 and 633 nm lasers respectively.

As used herein, "conjugated" means two entities stably bound to one another by any physicochemical means. It is important that the nature of the attachment is such that it does not substantially impair the effectiveness of either entity. Keeping these parameters in mind, any covalent or non-covalent linkage known to those of ordinary skill in the art is contemplated unless explicitly stated otherwise herein. Non-covalent conjugation includes hydrophobic interactions, ionic interactions, high affinity interactions such as biotin-avidin and biotin-streptavidin complexation and other affinity interactions. Such means and methods of attachment are known to those of ordinary skill in the art. Conjugation can be performed using standard techniques common to those of ordinary skill in the art. For example, U.S. Pat. Nos. 3,940,475 and 3,645,090 demonstrate conjugation of fluorophores and enzymes to antibodies.

The various components described herein can be conjugated to each other by any mechanism known in the art. For instance, functional groups which are reactive with various labels include, but are not limited to, (functional group: reactive group of light emissive compound) activated ester:amines or anilines; acyl azide:amines or anilines; acyl halide: amines, anilines, alcohols or phenols; acyl nitrile:alcohols or phenols; aldehyde:amines or anilines; alkyl halide:amines, anilines, alcohols, phenols or thiols; alkyl sulfonate:thiols, alcohols or phenols; anhydride:alcohols, phenols, amines or anilines; aryl halide:thiols; aziridine:thiols or thioethers; carboxylic acid:amines, anilines, alcohols or alkyl halides; diazoalkane:carboxylic acids; epoxide:thiols; haloacetamide: thiols; halotriazine:amines, anilines or phenols; hydrazine: aldehydes or ketones; hydroxyamine:aldehydes or ketones; imido ester:amines or anilines; isocyanate:amines or anilines; and isothiocyanate:amines or anilines.

The primary analyte-specific binding partners can be conjugated to the polymer and the detectable labels can be conjugated to all suitable components of the system by covalent or non-covalent means, whether directly or indirectly. Linkers and/or spacers may be used in some instances.

Linkers can be any of a variety of molecules, preferably nonactive, such as nucleotides or multiple nucleotides, straight or even branched saturated or unsaturated carbon chains of $C_1$-$C_{30}$, phospholipids, amino acids, and in particular glycine, and the like, whether naturally occurring or synthetic. Additional linkers include alkyl and alkenyl carbonates, carbamates, and carbamides. These are all related and may add polar functionality to the linkers such as the $C_1$-$C_{30}$ previously mentioned. As used herein, the terms linker and spacer are used interchangeably.

A wide variety of spacers can be used, many of which are commercially available, for example, from sources such as Boston Probes, Inc. (now Applied Biosystems). Spacers are not limited to organic spacers, and rather can be inorganic also (e.g., —O—Si—O—, or O—P—O—). Additionally, they can be heterogeneous in nature (e.g., composed of organic and inorganic elements). Essentially, any molecule having the appropriate size restrictions and capable of being linked to the various components such as fluorophore and probe can be used as a linker. Examples include the E linker (which also functions as a solubility enhancer), the X linker which is similar to the E linker, the O linker which is a glycol linker, and the P linker which includes a primary aromatic amino group (all supplied by Boston Probes, Inc., now Applied Biosystems). Other suitable linkers are acetyl linkers, 4-aminobenzoic acid containing linkers, Fmoc linkers, 4-aminobenzoic acid linkers, 8-amino-3,6-dioxactanoic acid linkers, succinimidyl maleimidyl methyl cyclohexane carboxylate linkers, succinyl linkers, and the like. Another example of a suitable linker is that described by Haralambidis et al. in U.S. Pat. No. 5,525,465, issued on Jun. 11, 1996.

The length of the spacer can vary depending upon the application and the nature of the components being conjugated (e.g., the polymer and the primary analyte-specific binding partner and the distance that can be tolerated between target sites on a polymer).

The conjugations or modifications described herein employ routine chemistry, which is known to those skilled in the art of chemistry. The use of linkers such as mono- and hetero-bifunctional linkers is documented in the literature (e.g., Herman-Son, 1996) and will not be repeated here.

The linker molecules may be homo-bifunctional or heterobifunctional cross-linkers, depending upon the nature of the molecules to be conjugated. Homo-bifunctional cross-linkers have two identical reactive groups. Hetero-bifunctional cross-linkers are defined as having two different reactive groups that allow for sequential conjugation reaction. Various types of commercially available cross-linkers are reactive with one or more of the following groups: primary amines, secondary amines, sulphydryls, carboxyls, carbonyls and carbohydrates. Examples of amine-specific cross-linkers are bis (sulfosuccinimidyl) suberate, bis[2-(succinimidooxycarbonyloxy)ethyl]sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Cross-linkers reactive with sulfhydryl groups include bismaleimidohexane, 1,4-di-[3'-(2'-pyridyldithio)-propionamido)] butane, 1-[p-azidosalicylamido]-4-[iodoacetamido]butane, and N-[4-(p- azidosalicylamido) butyl]-3'-[2'-pyridyldithio]propionamide. Cross-linkers preferentially reactive with carbohydrates include azidobenzoyl hydrazine. Cross-linkers preferentially reactive with carboxyl groups include 4-[p-azidosalicylamido]butylamine. Heterobifunctional cross-linkers that react with amines and sulfhydryls include N-succinimidyl-3-[2-pyridyldithio]propionate, succinimidyl [4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[3-dimethylaminopropyl]-carbodiimide hydrochloride. Heterobifunctional cross-linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio]propionyl hydrazide. The cross-linkers are bis-[β-4-azidosalicylamido) ethyl]disulfide and glutaraldehyde.

Amine or thiol groups may be added at any nucleotide of a synthetic nucleic acid so as to provide a point of attachment for a bifunctional cross-linker molecule. The nucleic acid may be synthesized incorporating conjugation-competent reagents such as Uni-Link AminoModifier, 3'-DMT-C6-Amine-ON CPG, AminoModifier II, N-TFA-C6-Amino-Modifier, C6-ThiolModifier, C6-Disulfide Phosphoramidite and C6-Disulfide CPG (Clontech, Palo Alto, Calif.).

Non-covalent methods of conjugation may also be used to bind the primary analyte-specific binding partner to the polymer or a detectable label to a probe, a polymer or an analyte-specific binding partner, for example. Non-covalent conjugation includes hydrophobic interactions, ionic interactions, high affinity interactions such as biotin-avidin and biotin-streptavidin complexation and other affinity interactions. As an example, a molecule such as avidin may be attached the nucleic acid, and its binding partner biotin may be attached to the primary analyte-specific antibody.

In some instances, it may be desirable to use a linker or spacer comprising a bond that is cleavable under certain conditions. For example, the bond can be one that cleaves under normal physiological conditions or that can be caused to cleave specifically upon application of a stimulus such as light, whereby the primary analyte-specific binding partner is released leaving the polymer intact. Readily cleavable bonds include readily hydrolyzable bonds, for example, ester bonds, amide bonds and Schiff's base-type bonds. Bonds which are cleavable by light are known in the art.

The polymers may be analyzed using a single molecule analysis system (e.g., a single polymer analysis system). A single molecule detection system is capable of analyzing single molecules separately from other molecules. Such a system may be capable of analyzing single molecules either in a linear manner and/or in their totality. In certain embodiments in which detection is based predominately on the presence or absence of a signal, linear analysis may not be required. However, there are other embodiments embraced by the invention which would benefit from the ability to linearly analyze molecules (preferably nucleic acids) in a sample. These include applications in which the sequence of the nucleic acid is desired, or in which the polymers are distinguished based on spatial labeling pattern rather than a unique detectable label.

Thus, the polymers can be analyzed using linear polymer analysis systems. A linear polymer analysis system is a system that analyzes polymers such as nucleic acids, in a linear manner (i.e., starting at one location on the polymer and then proceeding linearly in either direction therefrom). As a polymer is analyzed, the detectable labels attached to it are detected in either a sequential or simultaneous manner. When detected simultaneously, the signals usually form an image of the polymer, from which distances between labels can be determined. When detected sequentially, the signals are viewed in histogram (signal intensity vs. time) that can then be translated into a map, with knowledge of the velocity of the polymer. It is to be understood that in some embodiments, the polymer is attached to a solid support, while in others it is free flowing. In either case, the velocity of the polymer as it moves past, for example, an interaction station or a detector, will aid in determining the position of the labels relative to each other and relative to other detectable markers that may be present on the polymer.

An example of a suitable system is the GeneEngine™ (U.S. Genomics, Inc., Woburn, Mass.). The Gene Engine™ system is described in PCT patent applications WO98/35012 and WO00/09757, published on Aug. 13, 1998, and Feb. 24, 2000, respectively, and in issued U.S. Pat. No. 6,355,420 B1, issued Mar. 12, 2002. The contents of these applications and patent, as well as those of other applications and patents, and references cited herein are incorporated by reference herein in their entirety. This system is both a single molecule analysis system and a linear polymer analysis system. It allows, for example, single nucleic acids to be passed through an interaction station in a linear manner, whereby the nucleotides in the nucleic acid are interrogated individually in order to determine whether there is a detectable label conjugated to the nucleic acid. Interrogation involves exposing the nucleic acid to an energy source such as optical radiation of a set wavelength. The mechanism for signal emission and detection will depend on the type of label sought to be detected, as described herein.

This system comprises an optical source for emitting optical radiation; an interaction station for receiving the optical radiation and for receiving a polymer that is exposed to the optical radiation to produce detectable signals; and a processor constructed and arranged to analyze the polymer based on the detected radiation including the signals.

In one embodiment, the interaction station includes a localized radiation spot. In a further embodiment, the system further comprises a microchannel that is constructed to receive and advance the polymer through the localized radiation spot, and which optionally may produce the localized radiation spot. In another embodiment, the system further comprises a polarizer, wherein the optical source includes a laser constructed to emit a beam of radiation and the polarizer is arranged to polarize the beam. While laser beams are intrinsically polarized, certain diode lasers would benefit from the use of a polarizer. In some embodiments, the localized radiation spot is produced using a slit located in the interaction station. The slit may have a slit width in the range of 1 nm to 500 nm, or in the range of 10 nm to 100 nm. In some embodiments, the polarizer is arranged to polarize the beam prior to reaching the slit. In other embodiments, the polarizer is arranged to polarize the beam in parallel to the width of the slit.

In yet another embodiment, the optical source is a light source integrated on a chip. Excitation light may also be delivered using an external fiber or an integrated light guide. In the latter instance, the system would further comprise a secondary light source from an external laser that is delivered to the chip.

The analysis may also comprise generating optical radiation of a known wavelength to produce a localized radiation spot; passing a polymer through a microchannel; irradiating the polymer at the localized radiation spot; sequentially detecting radiation resulting from interaction of the polymer with the optical radiation at the localized radiation spot; and analyzing the polymer based on the detected radiation.

In one embodiment, the method further employs an electric field to pass the polymer through the microchannel. In another embodiment, detecting includes collecting the signals over time while the polymer is passing through the microchannel.

The systems described herein will encompass at least one detection system. The nature of such detection systems will depend upon the nature of the detectable label. The detection system can be selected from any number of detection systems known in the art. These include an electron spin resonance (ESR) detection system, a charge coupled device (CCD) detection system, a fluorescent detection system, an electrical detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system, many of which are electromagnetic detection systems.

Other single molecule nucleic acid analytical methods which involve elongation of DNA molecules can also be used in the methods of the invention. These include fiber-fluorescence in situ hybridization (fiber-FISH) (Bensimon, A. et al., Science 265(5181): 2096-2098 (1997)). In fiber-FISH, nucleic acid molecules are elongated and fixed on a surface by molecular combing. Hybridization with fluorescently labeled probe sequences allows determination of sequence landmarks on the nucleic acid molecules. The method requires fixation of elongated molecules so that molecular lengths and/or distances between markers can be measured. Pulse field gel electrophoresis can also be used to analyze the labeled nucleic acid molecules. Pulse field gel electrophoresis is described by Schwartz, D. C. et al., Cell 37(1): 67-75 (1984). Other nucleic acid analysis systems are described by Otobe, K. et al., Nucleic Acids Res. 29(22): E109 (2001), Bensimon, A. et al. in U.S. Pat. No. 6,248,537, issued Jun. 19, 2001, Herrick, J. et al., Chromosome Res. 7(6): 409: 423 (1999), Schwartz in U.S. Pat. No. 6,150,089 issued Nov. 21, 2000 and U.S. Pat. No. 6,294,136, issued Sep. 25, 2001. Other linear polymer analysis systems can also be used, and the invention is not intended to be limited to solely those listed herein.

Optical detectable signals are generated, detected and stored in a database. The signals can be analyzed to determine structural information about the nucleic acid. The signals can be analyzed by assessing the intensity of the signal to determine structural information about the nucleic acid. The computer may be the same computer used to collect data about the nucleic acids, or may be a separate computer dedicated to data analysis. A suitable computer system to implement embodiments of the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism. Computer programs for data analysis of the detected signals are readily available from CCD (charge coupled device) manufacturers.

The present invention is further illustrated by the following Examples, which in no way should be construed as further limiting. The entire contents of all of the references (including literature references, issued patents, published patent applications, and co-pending patent applications) cited throughout this application are expressly incorporated by reference herein.

EXAMPLES

Example 1

Comparison with Luminex® Liquid Array System

The pathogen detection system based on Luminex® liquid array and flow cytometer is compared to the system of the invention. Luminex® reportedly provides a multiplexing factor of 100 and detects proteins concentrations as low as 10 pM [1]. It reportedly can be used to detect pathogenic organisms such as bacteria and viruses. Although it reportedly can interrogate several thousands of beads per second using the Luminex® LX-100 (Luminex Corp., Austin, Tex.) flow cytometer, overall analysis time is restricted by the interaction of bead-immobilized antibodies with the antigens dissolved in analyzed solution. This time is at least 30 minutes and can be even longer if higher sensitivity is required.

The system described herein is designed for identification and quantification of multiple analytes such as but not limited to pathogens using single molecule polymer (e.g., DNA) mapping. It can be used to detect any substance against which binding partners (e.g., antibodies) are available or can be generated. It can also use other molecular recognition systems such as oligonucleotide-driven recognition of nucleic acids. The system can be applied to organic and biological molecules such as proteins, peptide toxins, and oligonucleotides as well as pathogens such as viruses, but it is not so limited.

Multiplexing. The proposed system has an unlimited multiplexing capability. The number of identifiable analytes is restricted only by the throughput rate of interrogation system used.

The extent of multiplexing is determined by the number of sites on the polymer that can be resolved. For example, the GeneEngine™ platform with 10 kHz interrogation frequency and single-fluorophore sensitivity can be used to achieve resolutions of 5 kb. Assume that twice that distance is allotted per single site (10 kb per site) in order to include the specific sequence (and/or probe length) as well as a gap to simplify the detection of the probe. Assume further that the stretched nucleic acid polymer is 200 kb in length. This DNA would include N=20 sequence sites suitable for detection. Thus, the total number of possible combinations (i.e., degree of multiplexing) for this DNA is $B=2^N=2^{20}=10^6$. Assume further that the orientations of the detected DNA molecules cannot be resolved (i.e., it is not known if a given readout represents a head-first or tail-first configuration). This would render only half of the detected barcodes as usable. However, if the barcodes are symmetrical, then they are uniquely identifiable regardless of the DNA orientation. There are $2^M=2^{N/2}$ symmetric barcodes for even N(N=2M) or $2^{M+1}$ for odd N(N=2M+1). Therefore, the total number of usable barcodes for even N(N=20) is $B=(2^N-2^{N/2})/2+2^{N/2}=(2^N+2^{N/2})/2=2^{N/2}(2^{N/2}+1)/2 \approx 2^{N-1}=2^{19}=5.2*10$, which is more than sufficient for any desired application.

The extent of multiplicity can be even greater with better resolution. The GeneEngine™ platform can also be used to achieve resolution at the level of 3 kb in some instances.

Following the same analysis as above, this would create sequence specific sites that are 6 kb in length and accordingly 200 kb DNA would include 33 sites, and the total number of usable barcodes is $B=2^{32}=4*10^9$.

For multiplexing similar to the Luminex®-based system, which is 100 [1], using a 10 kb site, an DNA 80 kb in length is sufficient (N=8, B=128). A DNA of this length (80 kb) has a contour length $L_c$=80 kb*0.34 µm/kb=27.2 µm.

Performance time. The performance time is limited by the time of incubation of the probes with the analyzed solution particularly if the concentration of antigens is low. In some embodiments, the system is used to detect and quantitate analytes that are hundreds of nanometers in size or smaller. In these latter instances, the hybridization rate will be determined by diffusion of the analytes. The interrogation rate of the GeneEngine™ platform is about 100 per second for DNA molecules of this size and total time needed for interrogation is several minutes.

Linearity. At high concentrations of analytes, the kinetic rate of their interaction with bead-immobilized antibodies can decrease by two orders of magnitude because of close proximity of primary antibodies immobilized on a rigid support [4]. Therefore, using a protocol with fixed incubation time, the concentration of an analyte can be underestimated at the upper end of the concentration range. While present in the Luminex® system, this artifact is not present in the system described herein because of the flexibility of the DNA polymer.

Sensitivity. The Luminexg system uses beads with 5.5 µm diameter. If they are interrogated with tightly focused excitation light (e.g., at the diffraction limit, the size of the spot is about 0.5 µm), most of the bound secondary antibodies will be not illuminated and therefore will not be included in the analysis. If the excitation volume is increased to encompass the whole bead, then (a) a more powerful laser is needed to ensure the same excitation intensity and (b) the noise increases proportionally to the volume [5]. Moreover, fluorophores not fully exposed to the laser (because of the presence of the bead) will be excited less intensely, and their fluorescence will be collected less effectively due to light scattering by the bead.

In the system of the invention, the DNA-analyte complex is stretched during interrogation and its cross-section does not exceed the size of the largest analyte. Therefore, the interrogation can be performed with a focused laser beam, representing a volume with 0.5 µm diameter. In more dilute conditions the signal is provided by a single fluorophore. Although the signal is less intense, it is still expected to be greater than that of the Luminex® system due to bead induced attenuation in the latter system. In addition, the background noise N is $(5.5/0.5)^3=1.3*10^3$ times greater in the Luminex® system. Therefore, the system of the invention has sensitivity or S/N ratio at least 1,000 times better than Luminex® system. These disadvantages in the Luminex® system cannot be overcome by using smaller bead sizes.

Scaling: Coiled form vs. stretched conformation. An important feature of the system of the invention is the use of a flexible polymer (i.e., it is in a compact (e.g., random coil) form during incubation and in stretched (e.g., linear) form during interrogation). Multiplicity can be increased by increasing the length of the polymer. However, the rate of increase should be controlled since multiplicity increases as a power function $\sim 2^L$. If the polymer is made twice as long (e.g., 160 kb and N=16), then the degree of multiplicity increases from 128 to 131,072 (or 1,024 times). Doubling the length of a DNA polymer does not change the parameters of the microfluidic chip or interrogation system because the cross-section of stretched DNA polymer is the same regardless of its length. More importantly, the illuminated volume and therefore noise and sensitivity remain the same. At the same time, the size of the coil will increase only $(2)^{1/2}=1.4$ times, and this will not practically influence the incubation system parameters. In contrast, multiplexing in the Luminex® system is proportional to bead volume. Increasing the bead diameter by 1.4 times (i.e., analogous to doubling the length of the DNA polymer), would increase the multiplicity by only $(1.4)^3=2.7$ times. This would additionally also simultaneously decrease the sensitivity by the same factor.

REFERENCES

1. McBride, M. T., Gammon, S., Pitesky, M., O'Brien, T., Smith, T., Aldrich, J., Langlois, R. G., Colston, B. & Venkateswaran, K. S. (2003) *Anal. Chem.* 75, 1924-1930.
2. Sinden, R. R. (1994) *DNA Structure and Function* (Academic Press, San Diego).
3. Dittrich, P. & Petra, S. (2002) *Biophys. J.* 82, 43a.
4. van Oss, C. J. (1997) *J. Mol. Recognit.* 10, 203-218.
5. Eigen, M. & Rigler, R. (1994) *Proc. Natl. Acad. Sci. U.S.A.* 91, 5740-5747.

EQUIVALENTS

It should be understood that the preceding is merely a detailed description of certain embodiments. It therefore should be apparent to those of ordinary skill in the art that various modifications and equivalents can be made without departing from the spirit and scope of the invention, and with no more than routine experimentation.

All references, patents and patent applications that are recited in this application are incorporated by reference herein in their entirety.

What is claimed is:

1. A method for detecting an analyte in a sample comprising
    contacting a sample with a polymer having bound to it a plurality of analyte-specific binding partners,
    detecting binding of an analyte to at least one of the plurality of analyte-specific binding partners, and
    determining a labeling pattern of the polymer while the plurality of analyte-specific binding partners is bound to the polymer,
    wherein the labeling pattern of the polymer is a spatial pattern of detectable labels along the length of the polymer that indicates the identity of the analyte, and wherein the polymer is a non-naturally occurring nucleic acid.

2. The method of claim 1, wherein the analyte is a plurality of analytes, the polymer is a plurality of polymers, and the analyte-specific partner is a plurality of analyte-specific polymers.

3. The method of claim 1, wherein the analyte-specific binding partner is an antibody.

4. The method of claim 1, wherein binding of the analyte to the analyte specific binding partner is detected using a secondary analyte-specific binding partner.

5. The method of claim 4, wherein the secondary analyte-specific binding partner is conjugated to a detectable label.

6. The method of claim 4, wherein the analyte-specific binding partner and the secondary analyte-specific binding partner is each labeled with a member of a FRET pair.

7. The method of claim 1, wherein the analyte is directly detectable and binding of the analyte to the analyte-specific binding partner is directly detected.

8. The method of claim 1, wherein the labeling pattern of the polymer is a spatial pattern of one or more sequence-specific probes bound along the length of the polymer.

9. The method of claim 1, wherein the detectable labels are conjugated to one or more sequence-specific probes.

10. The method of claim 1, wherein the detectable labels are incorporated into the polymer.

11. The method of claim 1, further comprising quantifying analyte concentration in the sample by determining an amount of analyte bound to the plurality of analyte-specific binding partners and comparing with a standard curve.

12. The method of claim 1, further comprising harvesting an analyte-bound polymer.

13. The method of claim 12, further comprising analyzing the analyte bound to the polymer.

14. The method of claim 1, wherein the analyte is a nucleic acid, a carbohydrate, a protein, a peptide, a lipid, a toxin, a cell, a spore, a cellular fragment or a spore fragment.

15. The method of claim 1, wherein the polymer is elongated prior to or simultaneously with determining the labeling pattern of the polymer.

16. The method of claim 1, wherein the labeling pattern of the polymer is a spatial pattern of analyte-specific binding partners bound along the length of the polymer.

17. The method of claim 1, wherein the labeling pattern of the polymer is determined using a focused flow through an electric field.

18. A method for detecting an analyte in a sample comprising contacting a sample with a polymer having bound to it an analyte-specific binding partner, detecting binding of an analyte to the analyte-specific binding partner, and determining a labeling pattern of the polymer while the plurality of analyte-specific binding partners is bound to the polymer, wherein the labeling pattern of the polymer indicates the identity of the analyte, and the polymer is a non-naturally occurring nucleic acid that is at least 80 kilobases in length.

19. A method for detecting an analyte in a sample comprising contacting a sample with a polymer having bound to it a plurality of analyte-specific binding partners, detecting binding of an analyte to at least one of the plurality of analyte-specific binding partners, and determining a labeling pattern of the polymer while the plurality of analyte-specific binding partners is bound to the polymer, wherein the polymer is a non-naturally occurring nucleic acid, the labeling pattern of the polymer is a spatial pattern of analyte-specific binding partners bound along the length of the polymer or one or more sequence-specific probes bound along the length of the polymer, and the labeling pattern of the polymer indicates the identity of the analyte.

* * * * *